United States Patent
Yokoi et al.

(10) Patent No.: US 9,963,483 B2
(45) Date of Patent: May 8, 2018

(54) PROCESS FOR PRODUCING SELF-ASSEMBLING PEPTIDE DERIVATIVES

(71) Applicant: MENICON CO., LTD., Nagoya-shi (JP)

(72) Inventors: Hidenori Yokoi, Kasugai (JP); Yasuhiro Yokoyama, Kasugai (JP); Keisuke Matsuyama, Kobe (JP); Kenichiro Yamamoto, Tatsuno (JP); Kinsei Anzai, Osaka (JP); Daisuke Nakamura, Tatsuno (JP); Toyohiro Nagano, Tatsuno (JP); Kazuya Kodama, Tatsuno (JP)

(73) Assignee: MENICON CO., LTD., Nagoya-Shi (JP)

( * ) Notice: Subject to any disclaimer, the term of this patent is extended or adjusted under 35 U.S.C. 154(b) by 19 days.

(21) Appl. No.: 14/412,190

(22) PCT Filed: Jul. 12, 2013

(86) PCT No.: PCT/JP2013/069124
§ 371 (c)(1),
(2) Date: Dec. 30, 2014

(87) PCT Pub. No.: WO2014/010721
PCT Pub. Date: Jan. 16, 2014

(65) Prior Publication Data
US 2015/0175663 A1 Jun. 25, 2015

(30) Foreign Application Priority Data
Jul. 13, 2012 (JP) .................................. 2012-157090

(51) Int. Cl.
| | | |
|---|---|---|
| A61K 38/00 | (2006.01) | |
| C07K 7/08 | (2006.01) | |
| C07K 7/06 | (2006.01) | |
| C07K 5/093 | (2006.01) | |
| C07K 5/083 | (2006.01) | |
| C07K 5/072 | (2006.01) | |
| C07K 5/062 | (2006.01) | |

(52) U.S. Cl.
CPC ................ *C07K 7/08* (2013.01); *A61K 38/00* (2013.01); *C07K 7/06* (2013.01); *C07K 5/06043* (2013.01); *C07K 5/06095* (2013.01); *C07K 5/0808* (2013.01); *C07K 5/0819* (2013.01)

(58) Field of Classification Search
None
See application file for complete search history.

(56) References Cited

U.S. PATENT DOCUMENTS

| | | | | |
|---|---|---|---|---|
| 8,299,032 B2 * | 10/2012 | Yokoi | ...................... | C07K 7/08 514/21.4 |
| 8,470,964 B2 | 6/2013 | Berezin et al. | | |
| 8,729,032 B2 * | 5/2014 | Nagai | ..................... | A61L 15/60 514/21.4 |
| 2005/0084902 A1 | 4/2005 | Nokihara et al. | | |
| 2011/0098225 A1 | 4/2011 | Berezin et al. | | |
| 2012/0058066 A1 | 3/2012 | Nagai et al. | | |
| 2013/0101662 A1 | 4/2013 | Carreno Rama et al. | | |

FOREIGN PATENT DOCUMENTS

| | | |
|---|---|---|
| JP | 2011-504888 A | 2/2011 |
| WO | WO-2002090985 | 11/2002 |
| WO | WO-2010103887 A1 | 9/2010 |
| WO | WO-2011015241 A1 | 2/2011 |
| WO | WO-2011047868 A2 | 4/2011 |

OTHER PUBLICATIONS

Bray, Nature Reviews|Drug Discovery (2003) vol. 2, 587-593.*
The Bachem Technical Bulletin, "Peptide synthesis and Purification" available at http://www.bachem.com/?id=213[8/29/2017 accessed on Aug. 29, 2017 6:37:50 PM.*
Bachem Technical Bulletin, "Amino Acid Derivatives and Resins" available at http://www.bachem.com/service-support/faq/amino-acid-derivatives-and-resins/ accessed on Aug. 29, 2017 6:34:25 PM.*
Extended Search Report for EP Application No. 13816363.9-1408 dated Mar. 29, 2016.
Nyfeler, Peptide Synthesis via Fragment Condensation, *Methods in Molecular Biology, vol. 35, Peptide Synthesis Protocols*, pp. 303-316 (1994).
Bastin et al., Salt Selection and Optimisation Procedures for Pharmaceutical New Chemical Entities, *Organic Process Research & Development*, vol. 4, pp. 427-435 (2000).
Nagarkar et al., Synthesis and Primary Characterization of Self-Assembled Peptide-Based Hydrogels, *Methods in Molecular Biology*, vol. 474, pp. 61-77 (2008).
Kopecek et al., Peptide-directed self-assembly of hydrogels, *Acta Biomaterialia*, vol. 5, pp. 805-816 (2009).

(Continued)

*Primary Examiner* — Satyanarayana R Gudibande
(74) *Attorney, Agent, or Firm* — Marshall, Gerstein & Borun LLP

(57) ABSTRACT

An object of the present invention is to provide a process capable of producing a self-assembling peptide derivative that is useful in the fields of regenerative medicine and surgery in large quantities and in an economical and efficient manner. In particular, provided is a production process employing a combination of (i) a step of convergently constructing a sequence with use of a common repeating unit consisting of a specific amino acid sequence and (ii) a step of first isolating the peptide derivative as a disulfuric acid salt, a tetramethanesulfonic acid salt or a tetra(trifluoroacetic acid (TFA) salt), and then subjecting the peptide salt to a salt exchange reaction to yield a tetrahydrochloric acid salt.

16 Claims, No Drawings

(56) References Cited

OTHER PUBLICATIONS

International Search Report and Written Opinion for Application No. PCT/JP2013/069124 dated Oct. 15, 2013.
International Preliminary Report on Patentability for Application No. PCT/JP2013/069124 dated Jan. 13, 2015. English Translation.
Nobuo Izumiya et al., Peptide Gosei no Kiso to Jikken, Maruzen Co., Ltd., pp. 146-153 and 222-223 (1985).
Edited by The Japanese Biochemical Society, Shin Seikagaku Jikken Koza 1 Tanpakushitsu VI—Gosei Oyobi Hatsugen-, Kabushiki Kaisha Tokyo Kagaku Dojin, pp. 3-29 and 66-74 (1992).
Han et al., Recent development of peptide coupling reagents in organic synthesis, Tetrahedron, vol. 60, No. 11, pp. 2447-2467 (2004).
Nagai et al., The mechanical stimulation of cells in 3D culture within a self-assembling peptide hydrogel, Biomaterials, pp. 1044-1051 (2012).

* cited by examiner

PROCESS FOR PRODUCING SELF-ASSEMBLING PEPTIDE DERIVATIVES

This application contains, as a separate part of the disclosure, a Sequence Listing in computer-readable form which is incorporated by reference in its entirety and identified as follows: Filename: 49272_Seqlisting.txt; Size: 16,530 bytes, created: Jun. 2, 2017.

TECHNICAL FIELD

The present invention relates to a process for producing a self-assembling peptide capable of forming a high strength peptide gel.

BACKGROUND ART

Peptide gels formed of self-assembling peptide derivatives are known to be useful in the fields of regenerative medicine and surgery (Patent Literature 1). Peptide derivatives represented by the structural formulae: Ac-Arg-Leu-Asp-Leu-Arg-Leu-Ala-Leu-Arg-Leu-Asp-Leu-Arg-$NH_2$ (SEQ ID NO: 1) and Ac-Arg-Leu-Asp-Leu-Arg-Leu-Leu-Leu-Arg-Leu-Asp-Leu-Arg-$NH_2$ (SEQ ID NO:2) (wherein Ac represents an acetyl group; the same applies hereinafter) are disclosed therein as peptides having the most preferred amino acid sequences with terminal modifications.

The applications of the self-assembling peptide derivatives and gels thereof include, for example, substrates for cell culture; cosmetics such as skin care products and hair care products; medical products such as decubitus preparations, bone fillers, injectable agents for aesthetic, adjuvant to ophthalmic operation, artificial vitreous bodies, artificial lenses, joint lubricants, ophthalmic solutions, DDS substrates, and hemostats; water retention materials for moistening; desiccants; and coating agents for medical devices such as contact lenses (Patent Literature 1).

Synthetic processes for peptides are generally known to include chemical synthesis, enzymatic synthesis and recombinant synthesis.

Enzymatic synthesis has the advantages of being performed under mild reaction conditions and forming few by-products, and other advantages. Known methods of enzymatic synthesis utilize, for example, metallopeptidases (such as thermolysin), aminoacyl-tRNA synthetases, alanine ligases, nonribosomal peptide synthetases, or the like. However, enzymatic synthesis has some problems. For example, some of the enzymes used in conventional enzymatic synthesis are at high cost. In addition, the desired peptide design is not always achieved due to preferential substrate specificity of enzymes.

Recombinant synthesis is a process in which DNA containing a nucleotide sequence encoding a peptide of interest is prepared and then expressed in host cells or the like. The vectors used for gene expression and peptide synthesis are, for example, plasmids, baculovirus, or the like, which are selected depending on the type of cells to be used. However, recombinant synthesis also has some problems. For example, the vectors into which DNA has been introduced sometimes do not produce the exact peptide of interest.

Chemical synthesis is a process in which amino acids are chemically coupled stepwise one by one. Chemical synthesis is generally known to include liquid-phase synthesis and solid-phase synthesis. Solid-phase peptide synthesis is a process using a solid phase, for example, polystyrene polymer gel beads about 0.1 mm in diameter having an amino group attached to the surface, and from the attached amino group, an amino acid chain is elongated by one amino acid each time through dehydration reaction. At the end of the synthesis of the desired peptide sequence, the peptide is cut off from the solid-phase surface to give a substance of interest. Solid-phase peptide synthesis allows the synthesis of ribosomal peptides, which are difficult to synthesize in bacteria, the incorporation of non-natural amino acids such as D-amino acids and heavy atom-substituted amino acids, the modification of peptide/protein backbone, and the like.

Solid-phase peptide synthesis is, however, inefficient because amino acids are coupled one by one at each synthesis step, and is also not economical because carriers for solid-phase synthesis are expensive and the amounts of reagents used are large. Further, scale-up of facilities is also difficult.

The peptide derivatives represented by the structural formulae: Ac-Arg-Leu-Asp-Leu-Arg-Leu-Ala-Leu-Arg-Leu-Asp-Leu-Arg-$NH_2$ (SEQ ID NO: 1) and Ac-Arg-Leu-Asp-Leu-Arg-Leu-Leu-Leu-Arg-Leu-Asp-Leu-Arg-$NH_2$ (SEQ ID NO:2), as disclosed in Patent Literature 1, are produced by conventional solid-phase synthesis. Hence there is a demand for the development of an efficient production process that allows reduction in the production cost of the peptide derivatives and scale-up of the production.

Each of the peptide derivatives, Ac-Arg-Leu-Asp-Leu-Arg-Leu-Ala-Leu-Arg-Leu-Asp-Leu-Arg-$NH_2$ (SEQ ID NO: 1) and Ac-Arg-Leu-Asp-Leu-Arg-Leu-Leu-Leu-Arg-Leu-Asp-Leu-Arg-$NH_2$ (SEQ ID NO:2), disclosed in Patent Literature 1 has four Arg residues (basic amino acid residues) and two Asp residues (acidic amino acid residues) within the sequence, and accordingly the peptide derivatives can be made into various salt forms. It is generally known that depending on the salt form of a peptide derivative, the functions and properties of the peptide derivative will change. Based on this, there is also a need for searching an appropriate salt form of the above peptide derivatives in order to satisfy the existing demands that the peptide derivatives should have, in addition to the function of dissolving in water to form a high strength peptide gel, certain properties such as easy handling and storage stability that are suitable for commercial production.

CITATION LIST

Patent Literature

Patent Literature 1: WO 2010/103887

SUMMARY OF INVENTION

Technical Problem

The most important object of the present invention is to provide a process capable of efficiently producing the above self-assembling peptide derivatives, which are useful in the fields of regenerative medicine and surgery, and of allowing reduction in the cost and scale-up of the production. Other objects of the present invention will be apparent from the description below.

Solution to Problem

The inventors conducted extensive study in order to solve the above problems, and as a result, found that among various salt forms of the self-assembling peptide derivatives, the tetrahydrochloric acid salt of the peptide derivatives is the optimal form in terms of the suitability for commercial production, the ease of handling, the storage stability, and the like. Further, the inventors established an efficient and robust process for producing the self-assembling peptide derivatives by combining (i) a step of convergently constructing a sequence with use of the peptide of the amino acid sequence mentioned below as a common repeating unit, focusing on the fact that both of the self-assembling peptide derivatives have the specific amino acid sequence, Arg-Leu-Asp-Leu-Arg (SEQ ID NO: 3), which appears twice in each of the formulae, and (ii) a step of first isolating the peptide derivative as a disulfuric acid salt, a tetramethanesulfonic acid salt or a tetra(trifluoroacetic acid (TFA) salt), and then subjecting the peptide salt to a salt exchange reaction to yield a tetrahydrochloric acid salt. The inventors also found that, when in a disulfuric acid salt form, the self-assembling peptide derivatives can be purified in a more efficient manner. Based on these new findings, the inventors conducted further study and completed the present invention. The detailed mechanism how the disulfuric acid salts of the peptide derivatives work advantageously is unknown, but it is assumed that separation from impurities at the time of precipitation proceeds advantageously.

That is, the present invention relates to the following.

[1] A disulfuric acid salt of a peptide derivative, represented by general formula (IX):

(SEQ ID NO: 4)
Ac-Arg-Leu-Asp-Leu-Arg-Leu-Ala-Leu-Arg-Leu-Asp-

Leu-Arg-NH$_2$•2H$_2$SO$_4$ or general formula (X):

(SEQ ID NO: 5)
Ac-Arg-Leu-Asp-Leu-Arg-Leu-Leu-Leu-Arg-Leu-Asp-

Leu-Arg-NH$_2$•2H$_2$SO$_4$.

[2] A process for producing a peptide derivative represented by general formula (VII):

(SEQ ID NO: 6)
Ac-Arg-Leu-Asp-Leu-Arg-Leu-Ala-Leu-Arg-Leu-Asp-

Leu-Arg-NH$_2$•n(acid)

(wherein n represents a number satisfying the equation: (the valence of the acid)×n=4, which number varies with the valence of the acid) or general formula (VIII):

(SEQ ID NO: 7)
Ac-Arg-Leu-Asp-Leu-Arg-Leu-Leu-Leu-Arg-Leu-Asp-

Leu-Arg-NH$_2$•n(acid)

(wherein n represents a number satisfying the equation: (the valence of the acid)×n=4, which number varies with the valence of the acid), the process comprising the steps of serially coupling, as building blocks, Peptide derivative I represented by general formula (I):

(SEQ ID NO: 8)
Arg(protecting group A)-Leu-Asp(protecting group B)-Leu-Arg(protecting group C)

(wherein protecting group A and protecting group C may be the same or different, and each is an Arg side-chain protecting group that is stable under basic conditions and can be removed under highly acidic conditions;

protecting group B is an Asp side-chain protecting group that is stable under basic conditions and can be removed under highly acidic conditions; and the amino group of the N-terminal Arg and/or the carboxy group of the C-terminal Arg may be modified) and Peptide derivative II represented by general formula (II):

Leu-X-Leu (wherein the amino group of the N-terminal Leu and/or the carboxy group of the C-terminal Leu may be modified; and X is Ala or Leu), removing the side-chain protecting groups with a strong acid, and optionally subjecting the coupling product to a terminal deprotection step, a modification step and/or a salt exchange step.

[3] The production process according to the above [2], comprising the steps of coupling Peptide derivative Ia corresponding to Peptide derivative I having an acetylated N-terminus with Peptide derivative IIa corresponding to Peptide derivative II having the C-terminus protected by an ester group to yield Peptide derivative IIIa, deprotecting the C-terminus of Peptide derivative IIIa, coupling the deprotected Peptide derivative IIIa with Peptide derivative Ib corresponding to Peptide derivative I having an amidated C-terminus to yield Peptide derivative IVa, and removing the side-chain protecting groups from Peptide derivative IVa.

[4] The production process according to the above [2], comprising the steps of coupling Peptide derivative Ia corresponding to Peptide derivative I having an acetylated N-terminus with Peptide derivative IIa corresponding to Peptide derivative II having the C-terminus protected by an ester group to yield Peptide derivative IIIa, deprotecting the C-terminus of Peptide derivative IIIa, coupling the deprotected Peptide derivative IIIa with Peptide derivative Ic corresponding Peptide derivative I having the C-terminus protected by an ester group to yield Peptide derivative IVb, removing the side-chain protecting groups from Peptide derivative IVb, and converting the C-terminal ester group to an amide group.

[5] The production process according to the above [3] or [4], wherein the C-terminal ester of Peptide derivative IIa is a methyl ester.

[6] The production process according to the above [4], wherein the C-terminal ester of Peptide derivative Ic is a methyl ester.

[7] The production process according to any one of the above [3] to [6], comprising the step of preparing Peptide derivative I by coupling Peptide derivative V represented by general formula (V):

```
Arg(protecting group A)-Leu
```

(wherein protecting group A is as defined above, and the N-terminus is modified) with
Peptide derivative VI represented by general formula (VI):

```
Asp(protecting group B)-Leu-Arg(protecting group
C)
```

(wherein protecting groups B and C are as defined above, and the C-terminus is modified), and
optionally subjecting the resulting coupling product to a deprotection step and/or a modification step of the amino group of the N-terminal Arg and/or the carboxy group of the C-terminal Arg.

[8] The production process according to any one of the above [3] to [7], wherein protecting groups A and C are each a Pbf (2,2,4,6,7-pentamethyl-2,3-dihydrobenzofuran-5-sulfonyl) group.

[9] The production process according to any one of the above [3] to [8], wherein protecting group B is a t-butyl ester.

[10] The production process according to any one of the above [7] to [9], comprising the step of preparing Peptide derivative Ia corresponding to Peptide derivative I having an acetylated N-terminus by
coupling Peptide derivative Va corresponding to Peptide derivative V having an acetylated N-terminus with Peptide derivative VIa corresponding to Peptide derivative VI having the C-terminus protected by an ester group, and removing the C-terminal ester; and/or
the step of preparing Peptide derivative Ia by coupling Peptide derivative Vb corresponding to Peptide derivative V having the N-terminus protected by a protecting group other than an acetyl group with Peptide derivative VIa,
converting the N-terminal group to an acetyl group, and removing the C-terminal ester.

[11] The production process according to the above [10], wherein the C-terminal ester of Peptide derivative VIa is a methyl ester.

[12] The production process according to any one of the above [7] to [9], comprising the step of preparing Peptide derivative Ib corresponding to Peptide derivative I having an amidated C-terminus by
coupling Peptide derivative Vb corresponding to Peptide derivative V having the N-terminus protected by a protecting group other than an acetyl group with Peptide derivative VIb corresponding to Peptide derivative VI having an amidated C-terminus, and
deprotecting the N-terminus of the resulting coupling product.

[13] The production process according to any one of the above [7] to [9], comprising the step of preparing Peptide derivative Ic corresponding to Peptide derivative I having the C-terminus protected by an ester group by coupling Peptide derivative Vb corresponding to Peptide derivative V having the N-terminus protected by a protecting group other than an acetyl group with Peptide derivative VIa corresponding to Peptide derivative VI having the C-terminus protected by an ester group, and deprotecting the N-terminus of the resulting coupling product.

[14] A process for producing a tetrahydrochloric acid salt of a peptide derivative represented by general formula (XI):

```
                                              (SEQ ID NO: 9)
Ac-Arg-Leu-Asp-Leu-Arg-Leu-Ala-Leu-Arg-Leu-Asp-
Leu-Arg-NH₂•4HCI
``` or general formula (XII):

```
                                              (SEQ ID NO: 10)
Ac-Arg-Leu-Asp-Leu-Arg-Leu-Leu-Leu-Arg-Leu-Asp-
Leu-Arg-NH₂•4HCI,
``` the process comprising the step of performing a salt exchange reaction of a peptide derivative represented by general formula (VII):

```
                                              (SEQ ID NO: 6)
Ac-Arg-Leu-Asp-Leu-Arg-Leu-Ala-Leu-Arg-Leu-Asp-
Leu-Arg-NH₂•n(acid)
```

(wherein n represents a number satisfying the equation: (the valence of the acid)×n=4, which number varies with the valence of the acid, with the exception of the case where the acid is hydrochloric acid) and/or
general formula (VIII):

```
                                              (SEQ ID NO: 7)
Ac-Arg-Leu-Asp-Leu-Arg-Leu-Leu-Leu-Arg-Leu-Asp-
Leu-Arg-NH₂•n(acid)
```

(wherein n represents a number satisfying the equation: (the valence of the acid)×n=4, which number varies with the valence of the acid, with the exception of the case where the acid is hydrochloric acid)
by treating the peptide derivative with hydrochloric acid in the presence of an organic solvent.

[15] The production process according to the above [14], wherein the organic solvent is THF (tetrahydrofuran).

[16] The producing process according to any one of the above [2] to [15], wherein the n(acid) in the peptide derivative represented by general formula (VII) and/or general formula (VIII) is disulfuric acid.

In the present invention, the "modification" is not particularly limited and includes chemical conversion typically used in the conventional peptide field, for example, protection of the N-terminus and/or the C-terminus with a protecting group, acetylation of the N-terminus, and/or amidation of the C-terminus, as described later.

Advantageous Effects of Invention

The present invention enables the production of the above self-assembling peptide derivatives, which are useful in the fields of regenerative medicine and surgery, in large quantities and in an economical and efficient manner.

DESCRIPTION OF EMBODIMENTS

A preferred embodiment of the present invention is a process for producing a peptide derivative represented by general formula (VII) or (VIII), the process comprising the steps of serially coupling Peptide derivative I represented by general formula (I) and Peptide II represented by general formula (II) as building blocks, removing the side-chain protecting groups with a strong acid, and optionally subjecting the coupling product to a salt exchange step, a terminal deprotection step, and/or a modification step.

The general formula (I) is

```
                                            (SEQ ID NO: 8)
Arg(protecting group A)-Leu-Asp(protecting group
B)-Leu-Arg(protecting group C),
``` wherein protecting group A and protecting group C may be the same or different, and each is an Arg side-chain protecting group that is preferably stable under basic conditions and can be removed under highly acidic conditions; and protecting group B is an Asp side-chain protecting group that is preferably stable under basic conditions and can be removed under highly acidic conditions. The basic conditions are usually at a pH of 8 to 11, and the highly acidic conditions are usually at a pH of 1 or less, preferably at a pH of −1 to 1. The amino group of the N-terminal Arg and/or the carboxy group of the C-terminal Arg may be modified.

The general formula (II) is

```
Leu-X-Leu
```

(wherein the amino group of the N-terminal Leu and/or the carboxy group of the C-terminal Leu may be modified; and X is Ala or Leu).

The general formula (VII) is

```
                                            (SEQ ID NO: 6)
Ac-Arg-Leu-Asp-Leu-Arg-Leu-Ala-Leu-Arg-Leu-Asp-
Leu-Arg-NH₂·n(acid)
```

(wherein n represents a number satisfying the equation: (the valence of the acid)×n=4, which number varies with the valence of the acid).

The general formula (VIII) is

```
                                            (SEQ ID NO: 7)
Ac-Arg-Leu-Asp-Leu-Arg-Leu-Leu-Leu-Arg-Leu-Asp-
Leu-Arg-NH₂·n(acid)
```

(wherein n represents a number satisfying the equation: (the valence of the acid)×n=4, which number varies with the valence of the acid).

The acid in the general formulae (VII) and (VIII) is not particularly limited, and may be an inorganic or organic acid. Examples of the inorganic acid include hydrochloric acid, phosphoric acid, hydrobromic acid, sulfuric acid, etc. Examples of the organic acid include acetic acid, formic acid, propionic acid, fumaric acid, maleic acid, succinic acid, tartaric acid, citric acid, malic acid, oxalic acid, benzoic acid, methanesulfonic acid, p-toluenesulfonic acid, benzenesulfonic acid, trifluoromethanesulfonic acid, trifluoroacetic acid, etc. Among these, preferred are hydrochloric acid, sulfuric acid, methanesulfonic acid and trifluoroacetic acid because of easiness of handling of the resulting salt of the peptide, production efficiency, and the like.

The peptide derivative of the present invention can be synthesized by various chemical synthetic methods, but is preferably synthesized by liquid-phase synthesis because of easiness of scale-up and cost efficiency.

In the present invention, the term "peptide" refers to a compound of amino acids covalently bonded together by peptide bonds. Peptides are two or often more amino acids bonded together. Peptide sequences are represented by formulae that are conventionally written with the N-terminus on the left and the C-terminus on the right.

In the present invention, the term "amino acid" is intended to denote any compound comprising at least one $NH_2$ group and at least one carboxy group. The amino acids of the present invention may be naturally or non-naturally occurring amino acids. Preferably, naturally occurring amino acids are used because they are available at a low cost and, by using them, peptide synthesis is easy to be carried out. Amino acid residues are abbreviated as follows: arginine is Arg; leucine is Leu; aspartic acid is Asp; and alanine is Ala.

In the present invention, the term "N-terminus" of a peptide is the end of the peptide chain terminated by a free amino group (—$NH_2$). The free amino group may be modified. On the other hand, the term "C-terminus" refers to the end of a peptide chain terminated by a free carboxy group (—COOH). The free carboxy group may be modified.

In the present invention, the term "coupling" refers to the reaction between the carboxy group of an amino acid or the C-terminus of a first peptide to the amino group of another amino acid or the N-terminus of a second peptide. In other words, during coupling, two peptide intermediate fragments, or a peptide intermediate fragment and a reactive amino acid, are coupled, generally, in an appropriate solvent, and usually in the presence of additional reagents that promote the efficiency of the coupling reaction. The additional reagent is, for example, a carboxylic acid activating agent as described later.

In the present invention, the term "building block" is intended to mean a short-chain peptide derivative used for the coupling reaction for the synthesis of a peptide derivative. The number of the amino acids contained in the short-chain peptide derivative is not particularly limited, and any peptide derivative made up of two or more amino acids bonded together is suitable as a building block. The building block can also be synthesized by coupling shorter peptide derivatives. Such a shorter peptide derivative used for the synthesis of the building block is also referred to as a "subunit" hereinafter.

In a preferred embodiment of the present invention, Peptide derivative I of general formula (I) is coupled with Peptide derivative II of general formula (II) to yield Peptide derivative III of general formula (III). The peptide derivative of general formula (III) is further coupled with Peptide derivative I of general formula (I), and the side-chain protecting groups are removed to synthesize Peptide derivative IV of general formula (IV).

The general formula (III) is

```
                                            (SEQ ID NO: 26)
Arg(protecting group A)-Leu-Asp(protecting group
B)-Leu-Arg(protecting group C)-Leu-X-Leu,
``` wherein protecting group A and protecting group C may be the same or different, and each is an Arg side-chain protecting group that is preferably stable under basic conditions and can be removed under highly acidic conditions; and protecting group B is an Asp side-chain protecting group that is preferably stable under basic conditions and can be removed under highly acidic conditions. The basic conditions are usually at a pH of 8 to 11, and the highly acidic conditions are usually at a pH of 1 or less, preferably at a pH of −1 to 1. X is Ala or Leu. The amino group of the N-terminal Arg and/or the carboxy group of the C-terminal Leu may be modified.

The general formula (IV) is (SEQ ID NO: 27)
Ac-Arg-Leu-Asp-Leu-Arg-Leu-X-Leu-Arg-Leu-Asp-Leu-Arg-NH$_2$, wherein X is Ala or Leu.

In another preferred embodiment of the present invention, the process comprises the step of coupling a subunit represented by general formula (V) with a subunit represented by general formula (VI) to synthesize the peptide derivative of general formula (I).

In the present invention, the "protecting group" is any sort of group that can prevent the atom (e.g., nitrogen or oxygen) or functional group (e.g., an amino group or carboxy group) to which it is attached from participating in undesired reactions during peptide synthesis and other processing. Protecting groups include protecting groups for the N-terminal amino group and/or the C-terminal carboxy group, and protecting groups for side-chain functional groups.

The Amino protecting group will be specifically illustrated below.

The amino protecting group is not particularly limited in the present invention and examples thereof include substituted or unsubstituted groups of aralkyloxycarbonyl type, such as benzyloxycarbonyl (Z), p-chlorobenzyloxycarbonyl, p-bromobenzyloxycarbonyl, p-nitrobenzyloxycarbonyl, p-methoxybenzyloxycarbonyl, benzhydryloxycarbonyl, 2-(p-biphenylyl)isopropyloxycarbonyl, 2-(3,5-dimethoxyphenyl) isopropyloxycarbonyl, p-phenylazobenzyloxycarbonyl, triphenylphosphonoethyloxycarbonyl, and 9-fluorenylmethyloxycarbonyl (Fmoc) groups; substituted or unsubstituted groups of alkyloxycarbonyl type, such as t-butyloxycarbonyl (Boc), t-amyloxycarbonyl, diisopropylmethyloxycarbonyl, isopropyloxycarbonyl, ethyloxycarbonyl, allyloxycarbonyl, 2-methylsulfonylethyloxycarbonyl, and 2,2,2-trichloroethyloxycarbonyl groups; groups of cycloalkyloxycarbonyl type, such as cyclopentyloxycarbonyl, cyclohexyloxycarbonyl, adamantyloxycarbonyl, and isobornyloxycarbonyl groups; and groups containing a hetero atom, such as benzenesulfonyl, p-toluenesulfonyl, mesitylenesulfonyl, methoxytrimethylphenylsulfonyl, 2-nitrobenzenesulfonyl, 2-nitrobenzenesulfenyl, 4-nitrobenzenesulfonyl, and 4-nitrobenzenesulfenyl groups.

Among these amino protecting groups, those comprising a carbonyl, a sulfenyl or a sulfonyl group are preferred. More preferred are allyloxycarbonyl, t-butyloxycarbonyl (Boc), benzyloxycarbonyl (Z), 9-fluorenylmethyloxycarbonyl (Fmoc), 2-nitrobenzenesulfonyl (Nosyl), 2-nitrobenzenesulfenyl (Nps) groups, and/or substituted derivatives thereof. Further more preferred are a Boc group and/or a Fmoc group.

The amino protecting group may be introduced or removed by various usual methods. The amino protecting group may be introduced by, for example, reaction of the amino group with suitable acid halides such as carbobenzoxy chloride or N-succinimidyl carbonates such as N-(fluorenylmethoxycarbonyloxy)succinimide. On the other hand, the amino protecting group may be removed by, for example, hydrogenolysis, treatment with dilute ammonium hydroxide or sodium hydroxide aqueous solution, treatment with sodium, treatment with sodium amide, treatment with hydrazine, or enzymatic hydrolysis.

A Boc group can be introduced or removed in accordance with conventional methods. For example, a Boc group can be introduced by reaction of an amino acid with di-tert-butyl dicarbonate (Boc$_2$O) in the presence of a base such as pyridine, triethylamine, sodium hydroxide aqueous solution and sodium carbonate aqueous solution. Deprotection can be carried out by means of an organic acid or an inorganic acid. Examples of the organic acid include trifluoroacetic acid (TFA), trifluoromethanesulfonic acid, formic acid, p-toluenesulfonic acid, and methanesulfonic acid; and examples of the inorganic acid include hydrochloric acid, phosphoric acid, hydrobromic acid, and sulfuric acid. Deprotection is preferably carried out by means of an inorganic acid, in particular HCl, preferably dissolved in an organic solvent.

A Fmoc group can be introduced or removed in accordance with conventional methods. For example, a Fmoc group can be introduced by reaction of an amino acid with a reagent such as fluorenylmethyl chloroformate (Fmoc-Cl) in the presence of a base such as pyridine, triethylamine and sodium hydrogen carbonate aqueous solution. Deprotection can be carried out by treatment with a secondary amine such as pyrrolidine, piperidine and morpholine in DMF or THF.

The protection of the carboxy group will be specifically illustrated below.

The protection of the carboxy group can generally be performed by esterification (protection by an ester group) or silylation (protection by a silyl group). The ester group is not particularly limited and examples thereof include lower alkyl ester groups, such as methyl ester, ethyl ester and tert-butyl ester (t-Bu) groups, and aralkyl ester groups, such as a benzyl ester group, a p-methoxybenzyl ester group and a p-nitrobenzyl ester group. The silyl group is not particularly limited and examples thereof include trialkylsilyl groups, such as trimethylsilyl, triethylsilyl, t-butyldimethylsilyl and i-propyl-dimethylsilyl groups. In the present invention, the protection is preferably carried out by esterification. More preferably, the C-terminal carboxy group of the peptide derivative is protected as a methyl ester and the side-chain carboxy group of the aspartic acid is protected as a t-Bu ester.

The esterification can be performed in accordance with conventional methods. For example, the esterification can be carried out using an acid catalyst or a condensing agent in an alcohol. The t-Bu ester can be formed by esterification using a condensing agent in tert-butyl alcohol, or can be synthesized by reaction of the carboxy group with isobutene using a sulfuric acid catalyst. The benzyl ester can be introduced by, for example, converting the carboxy group to its cesium salt and reacting the cesium salt with benzyl bromide.

Deprotection of the carboxy group can generally be carried out by hydrolysis, saponification, hydrogenolysis, enzymatic hydrolysis, or the like.

The protection of the arginine side-chain in the present invention will be illustrated below.

The guanidino group of the arginine side-chain is highly nucleophilic and can thus be protected by appropriate electron-withdrawing protecting groups such as sulfonyl, nitro, tosyl, and carbonyl groups. Preferred is protection by a sulfonyl group. The sulfonyl group is not particularly limited and examples thereof include 2,2,4,6,7-pentamethyl-2,3-dihydrobenzofuran-5-sulfonyl (Pbf), p-toluenesulfonyl (p-Ts), 4-methoxy-2,3,6-trimethylbenzenesulphonyl (Mtr) (M. Fujino et al., Chem. Pharm. Bull., 29, 2825 (1981)), 2,2,5,7,8-pentamethylchroman-6-sulfonyl (Pmc) (R. Ramage at al., Tetrahedron Lett., 28, 2287 (1987)), and 2-methoxybenzenesulfonyl groups. Preferably, a Pbf group is used in the present invention.

In the present invention, the "acetylation of the N-terminus" refers to the modification of the N-terminus with an acetyl group. The "conversion of the N-terminal group to an acetyl group" refers to the removal of the N-terminal amino protecting group other than an acetyl group, followed by the modification of the N-terminal amino group with an acetyl group. An acetyl group can be introduced in accordance with conventional methods. For example, an acetyl group can be introduced by reaction of the amino group with an acetylating reagent such as acetyl chloride and acetic anhydride in the presence of a base such as triethylamine, pyridine, and sodium hydroxide aqueous solution, in an organic solvent such as tetrahydrofuran (THF), dichloromethane (DCM), chloroform, carbon tetrachloride, ether, dioxane, benzene, toluene, and N,N-dimethylformamide (DMF).

In a preferred embodiment of the present invention, the synthesis and/or coupling of a peptide can be performed in the presence of a carboxylic acid activating agent.

Examples of the carboxylic acid activating agent that is useful in the present invention include carbodiimides, carbonyldiimidazoles, phosphonium salts, uronium salts, guanidinium salts, acyl halides, azides, symmetric anhydrides, mixed anhydrides, and active esters. Such a carboxylic acid activating agent may be used before the coupling step or used in situ prior to the introduction of the free amino peptide derivative.

The carboxylic acid activating agent is not particularly limited and examples thereof include carbodiimide reagents such as N,N'-dicyclohexylcarbodiimide (DCC), N-ethyl-N'-(3-dimethylaminopropyl)carbodiimide (EDC), and 1-(3-dimethylaminopropyl)-3-ethylcarbodiimide hydrochloride (EDCI also referred to as "WSC"); carbodiimidazole reagents such as 1,1'-carbonyldiimidazole (CDI), diisopropylcarbodiimide (DIPCDI), and diisopropylcarbodiimide (DIC) or derivatives thereof; phosphonium salts such as (benzotriazol-1-yloxy)tris(dimethylamino)phosphonium (BOP), benzotriazol-1-yl-oxytripyrrolidinophosphonium hexafluorophosphate (PyBOP), (7-azabenzotriazol-1-yloxy)tripyrrolidinophosphonium hexafluorophosphate (PyAOP), bromo-tris-pyrrolidinophosphonium hexafluorophosphate (PyBroP), and chloro-tris-pyrrolidinophosphonium hexafluorophosphate (PyCloP) or derivatives thereof; uronium or guanidinium salts such as o-benzotriazole-N,N,N',N'-tetramethyl-uronium-hexafluoro-phosphate (HBTU), o-(benzotriazol-1-yl)-N,N,N',N'-tetramethyluronium tetrafluoroborate (TBTU), 2-(7-aza-1H-benzotriazol-1-yl)-1,1,3,3-tetramethyluronium hexafluorophosphate (HATU), and O-(7-azabenzotriazol-1-yl)-1,1,3,3-bis(tetramethylene)uronium hexafluorophosphate (HAPyU) or derivatives thereof; acyl halides such as isobutyl chloroformate (iBCF), pivaloyl chloride (PivCl), t-butylchloroformate (TBCF), and ethyl chloroformate (ECF) or derivatives thereof; esterificating agents such as pentafluorophenol (PfP), and N-hydroxysuccinimide (NHS) or derivatives thereof; and azidination agents such as diphenylphosphoryl azide (DPPA) or derivatives thereof. Preactivated amino acids or under the form of N-carboxyanhydrides, and in particular urethane-N-carboxyanhydrides (UNCA) are also good examples of carboxylic acid activating agents.

The carboxylic acid activating agent is preferably one or more selected from the group consisting of carbodiimides, carbonyldiimidazoles, acyl halides, phosphonium salts, uronium salts and guanidinium salts, and is more preferably a carbodiimide.

When such a carboxylic acid activating agent is used, the coupling reaction is often carried out in the presence of a base as an additional reagent. In a preferred embodiment of the present invention, the coupling reaction is thus carried out in the presence of a base. The base is preferably one or more selected from the group consisting of tertiary and heteroaromatic amines, such as N-methylmorpholine (NMM), pyridine, triethylamine (TEA), and diisopropylethylamine (DIPEA). In view of reaction efficiency, more preferred is NMM and/or TEA.

In a preferred embodiment of the present invention, the peptide coupling reaction as described above is carried out in a polar organic solvent. The polar organic solvent is not particularly limited and examples thereof include N,N-dimethylacetamide (DMA), N,N-dimethylformamide (DMF), N-methylpyrrolidone (NMP), dimethylsulfoxide (DMSO), ethyl acetate (AcOEt), dichloromethane (DCM), pyridine, chloroform, acetonitrile, dimethoxyethane, dioxane, tetrahydrofuran (THF) and a mixtures thereof. In view of reaction efficiency, more preferred is DMF and/or THF.

In the present invention, the coupling reaction can generally be carried out at a temperature of −45° C. to +45° C. In order to increase reaction efficiency, the coupling reaction is preferably carried out at −25° C. to +35° C., more preferably −5° C. to +25° C.

In a preferred embodiment of the present invention, the process preferably comprises the step of preparing Peptide derivative III of general formula (III) by coupling Peptide derivative Ia corresponding to Peptide derivative I of general formula (I) having an acetylated N-terminus with Peptide derivative IIa corresponding to Peptide derivative II of general formula (II) having the C-terminus protected by an ester group to synthesize Peptide derivative IIIa, and deprotecting the C-terminus of Peptide derivative IIIa. The ester group at the C-terminus of Peptide derivative IIa is not particularly limited and any ester group can be selected. However, in view of easiness of handling etc., preferred is a methyl ester.

In another preferred embodiment of the present invention, the process comprises the step of preparing Peptide derivative IV of general formula (IV) by coupling Peptide derivative III of general formula (III) with Peptide derivative Ib corresponding to Peptide derivative I of general formula (I) having an amidated C-terminus to synthesize Peptide derivative IVa, and removing the side-chain protecting groups from Peptide derivative IVa.

In another preferred embodiment of the present invention, the process comprises the step of preparing Peptide derivative IV of general formula (IV) by coupling Peptide derivative III of general formula (III) with Peptide derivative Ic corresponding to Peptide derivative I of general formula (I) having the C-terminus protected by an ester group to synthesize Peptide derivative IVb, removing the side-chain protecting groups from Peptide derivative IVb, and amidating the C-terminus of the deprotected Peptide derivative IVb. The ester group at the C-terminus of Peptide derivative Ic is not particularly limited and any ester group can be selected. However, in view of easiness of handling etc., preferred is a methyl ester.

In another preferred embodiment of the present invention, the process comprises the step of preparing Peptide derivative Ia corresponding to Peptide derivative I of general formula (I) having an acetylated N-terminus by coupling Peptide derivative Va corresponding to Peptide derivative V of general formula (V) having an acetylated N-terminus with Peptide derivative VIa corresponding to peptide derivative VI of general formula (VI) having the C-terminus protected by an ester group to yield a peptide derivative, and deprotecting the C-terminus of the peptide derivative. The ester group at the C-terminus of Peptide derivative VIa is not particularly limited and any ester group can be selected. However, in view of easiness of handling etc., preferred is a methyl ester.

In another preferred embodiment of the present invention, the process comprises the step of preparing Peptide derivative Ia corresponding to Peptide derivative I of general formula (I) having an acetylated N-terminus by coupling Peptide derivative Vb corresponding to Peptide derivative V of general formula (V) having the N-terminal amino group protected by a protecting group other than an acetyl group with Peptide derivative VIa corresponding to Peptide derivative VI of general formula (VI) having the C-terminus protected by an ester group to yield a peptide derivative, converting the N-terminal group of the peptide derivative to an acetyl group (removing the N-terminal protecting group followed by acetylating), and deprotecting the C-terminus of the peptide derivative. The protecting group other than an acetyl group at the N-terminus is not particularly limited and may be any protecting group that can be removed without affecting protecting group A, protecting group B, protecting group C or the ester group (in cases where the deprotection of the C-terminus is performed after the conversion of the N-terminal group to an acetyl group). However, preferably the protecting group other than an acetyl group is one or more selected from the group consisting of Fmoc, Boc, benzyloxycarbonyl (Z), allyloxycarbonyl, 2-nitrobenzenesulfonyl (Nosyl) and 2-nitrobenzenesulfenyl (Nps) groups, and is more preferably a Fmoc and/or Boc group. The ester group at the C-terminus of Peptide derivative VIa is not particularly limited and any ester group can be selected. However, in view of easiness of handling etc., preferred is a methyl ester. The order of performing the conversion step of the N-terminal group to an acetyl group and the deprotection step of the C-terminus of the obtained peptide derivative after the coupling reaction is not particularly limited. The conversion of the N-terminal group to an acetyl group may precede the deprotection of the C-terminus, or alternatively, the deprotection of the C-terminus may precede the conversion of the N-terminal group to an acetyl group.

In another preferred embodiment of the present invention, the process comprises the step of preparing Peptide derivative Ib corresponding to Peptide derivative I of general formula (I) having an amidated C-terminus by coupling Peptide derivative Vb corresponding to Peptide derivative V of general formula (V) having the N-terminus protected by a protecting group other than an acetyl group with Peptide derivative VIb corresponding to Peptide derivative VI of general formula (VI) having an amidated C-terminus to yield a peptide derivative, and deprotecting the N-terminus of the peptide derivative. The protecting group other than an acetyl group at the N-terminus is not particularly limited and may be any protecting group that can be removed without affecting protecting group A, protecting group B, protecting group C or the amide group. However, in view of easiness of handling etc., preferably the protecting group other than an acetyl group is one or more selected from the group consisting of Fmoc, Boc, benzyloxycarbonyl (Z), allyloxycarbonyl, 2-nitrobenzenesulfonyl (Nosyl) and 2-nitrobenzenesulfenyl (Nps) groups, and is more preferably a Fmoc and/or Boc group.

In another preferred embodiment of the present invention, the process comprises the step of preparing Peptide derivative Ic corresponding to Peptide derivative I of general formula (I) having the C-terminus protected by an ester group by coupling Peptide derivative Vb corresponding to Peptide derivative V of general formula (V) having the N-terminal amino group protected by a protecting group other than an acetyl group with Peptide derivative VIa corresponding to Peptide derivative VI of general formula (VI) having the C-terminus protected by an ester group to yield a peptide derivative, and deprotecting the N-terminus of the peptide derivative. The protecting group other than an acetyl group at the N-terminus is not particularly limited and may be any protecting group that can be removed without affecting protecting group A, protecting group B, protecting group C or the ester group. However, in view of easiness of handling etc., preferably the protecting group other than an acetyl group is one or more selected from the group consisting of Fmoc, Boc, benzyloxycarbonyl (Z), allyloxycarbonyl, 2-benzenesulfonyl (Nosyl) and 2-nitrobenzenesulfenyl (Nps) groups, and is more preferably a Fmoc and/or Boc group. The ester group at the C-terminus of Peptide derivative VIa is not particularly limited and any ester group can be selected. However, in view of easiness of handling etc., preferred is a methyl ester.

The self-assembling peptide derivative in the form of a tetrahydrochloric acid salt was found to be easy to handle, highly stable during storage and soluble in water, and thus a tetrahydrochloric acid salt was found to be the optimal form. Accordingly, in a preferred embodiment of the present invention, the process preferably comprises the step of performing a salt exchange reaction of a salt such as a disulfuric acid salt, a tetra-TFA salt and a tetramethanesulfonic acid salt of the peptide derivative obtained after the removal of the amino acid side-chain protecting groups (i.e., the peptide derivative represented by general formula VII or VIII, with the exception of the case where the acid is hydrochloric acid), thereby yielding a tetrahydrochloric acid salt thereof.

In a preferred embodiment of the present invention, the form of the resulting salt (i.e., the peptide derivative represented by general formula VII or VIII) depends on the combination of the reagents (typically, TFA+a scavenger (an agent for capturing the cleaved protecting groups)) used for the removal of the side-chain protecting groups after the construction of the amino acid sequence. That is, the use of an 95 vol % aqueous TFA solution gives a disulfuric acid salt; the use of TFA/1,2-ethanedithiol/phenol/triisopropylsilane/thioanisole gives a tetra-TFA salt; and the use of TFA/methanesulfonic acid/triisopropylsilane gives a tetramethanesulfonic acid salt. These salts, particularly a disulfuric acid salt, are poorly soluble in a solvent, whereas impurities are easily soluble in a solvent. Consequently, a reaction product can be obtained with high purity. In cases where an aqueous TFA solution is used, the concentration is preferably 75 to 98 vol %. In cases where TFA/1,2-ethanedithiol/phenol/triisopropylsilane/thioanisole is used, the weight ratio is preferably (82 to 90)/(2 to 6)/(3 to 12)/(2 to 4)/(2 to 4). In cases where TFA/methanesulfonic acid/triisopropylsilane is used, the weight ratio is preferably (87 to 90)/(2 to 6)/(5 to 8). In cases where TFA/1,2-ethanedithiol/phenol/triisopropylsilane/thioanisole is used, preferred amounts of these reagents are as follows: 2 to 7 parts by weight of 1,2-ethanediol, 3 to 15 parts by weight of phenol, 2 to 5 parts by weight of triisopropylsilane and 2 to 5 parts by weight of thioanisole based on 100 parts by weight of TFA. In cases where TFA/methanesulfonic acid/triisopropylsilane is used, preferred amounts of these reagents are as follows: 2 to 7 parts by weight of methanesulfonic acid and 5 to 10 parts by weight of triisopropylsilane based on 100 parts by weight of TFA.

The salt exchange can be performed by various methods. The salt exchange may be performed by directly adding hydrochloric acid to the peptide derivative to be subjected to salt exchange, or by allowing hydrochloric acid to act on the peptide derivative to be subjected to salt exchange in the coexistence of a solvent. The solvent may be a protonic polar solvent or a non-protonic organic solvent. The protonic polar solvent is not particularly limited and examples thereof include water, secondary and tertiary alcohols, acetic acid, formic acid, etc. The non-protonic polar solvent is not particularly limited and examples thereof include N,N-dimethylacetamide (DMA), N,N-dimethylformamide (DMF), N-methylpyrrolidone (NMP), dimethylsulfoxide (DMSO), dichloromethane (DCM), chloroform, acetonitrile, dimethoxyethane, dioxane, tetrahydrofuran (THF), ethers, etc.

In a preferred embodiment of the present invention, the salt exchange reaction, which is the final step, is carried out not by reaction of the peptide derivative with hydrochloric acid alone but by reaction of the peptide derivative with hydrochloric acid in the coexistence of an organic solvent, and thereby efficiently yields a tetrahydrochloric acid salt. The solvent used is preferably a non-protonic polar solvent in view of the efficiency of the salt exchange reaction, and is more preferably THF (tetrahydrofuran). In cases where the salt exchange reaction is carried out in the coexistence of the organic solvent, the weight ratio of hydrochloric acid/organic solvent is preferably 80/20 to 60/40. The concentration of the hydrochloric acid used in this embodiment is not particularly limited and may be any appropriate concentration, for example, 0.05 to 5 N.

The reaction product can be isolated and purified by purification methods, such as extraction, crystallization, freeze-drying, spray-drying, sedimentation, and chromatography (for example, thin layer or column chromatography). A preferred isolation and purification method is sedimentation or crystallization. In one embodiment, at least one intermediate peptide or end product is isolated and purified by sedimentation or crystallization. In a particularly preferred embodiment of the process according to the present invention, most of the intermediates and end products are isolated and purified by sedimentation or crystallization, if desired.

EXAMPLES

The present invention will be more specifically illustrated with reference to Examples, but is not limited to these Examples. Various alterations are possible by a person having ordinary knowledge in the art, without departing from the technical idea of the present invention. The materials used in Examples and Reference Examples are easily produced by known methods and methods analogous to known methods.

The abbreviations employed in Examples and Reference Examples are defined as follows: Ac is acetyl group; —OMe is methyl ester; Ot-Bu is tert-butyl ester; Pbf is 2,2,4,6,7-pentamethyl-2,3-dihydrobenzofuran-5-sulfonyl; MsOH is methanesulfonic acid; TFA is trifluoroacetic acid; EDC is N-ethyl-N'-(3-dimethylaminopropyl)carbodiimide; NMM is N-methylmorpholine; TEA is triethylamine; MeOH is methanol; t-BuOH is tert-butyl alcohol; IPA is isopropyl alcohol; MTBE is methyl-t-butyl ether; THF is tetrahydrofuran; DMF is N,N-dimethylformamide; CPME is cyclopentyl methyl ether; IPE is isopropyl ether; Fmoc is 9-fluorenylmethyloxycarbonyl; Boc is t-butyloxycarbonyl; and HOBt is 1-hydroxybenzotriazole.

Example 1

Preparation of disulfuric acid salt of peptide derivative represented by general formula (IX):

(SEQ ID NO: 4)
Ac-Arg-Leu-Asp-Leu-Arg-Leu-Ala-Leu-Arg-Leu-Asp-
Leu-Arg-NH$_2$·2H$_2$SO$_4$ (1) Synthesis of Peptide Derivative IIIa (X=Ala):

(SEQ ID NO: 12)
Ac-Arg(Pbf)-Leu-Asp(Ot-Bu)-Leu-Arg(Pbf)-Leu-Ala-
Leu-OMe

In a 300 mL reaction container were placed 2.69 g (7.3 mmol) of Cl$^-$.H$_2^+$-Leu-Ala-Leu-OMe (a hydrochloric acid salt of Peptide derivative IIa (X=Ala)) and 1.05 g (7.8 mmol) of HOBt, and they were suspended in THF (38.2 mL). To this suspension, 1.96 g (10.2 mmol) of EDC.HCl was added. While the mixture was cooled in an ice bath, 2.52 g (24.9 mmol) of NMM was added dropwise. Separately, 7.65 g (6 mmol) of Ac-Arg(Pbf)-Leu-Asp(Ot-Bu)-Leu-Arg(Pbf)-OH (SEQ ID NO: 11) (Peptide derivative Ia) was dissolved in a mixed solvent of DMF (15.3 mL) and THF (22.9 mL). This solution was added dropwise to the previously prepared reaction suspension cooled in the ice bath. The mixture was stirred under cooling in the ice bath overnight. To this, 0.5 N hydrochloric acid (38 mL), THF (74 mL) and MTBE (46 mL) were added, and dispersion was performed at room temperature. Suction filtration and vacuum drying were performed to give 8.39 g of Ac-Arg(Pbf)-Leu-Asp(Ot-Bu)-Leu-Arg(Pbf)-Leu-Ala-Leu-OMe (SEQ ID NO:12) (Peptide derivative IIIa) as a white powder (88% yield from Ac-Arg(Pbf)-Leu-Asp(Ot-Bu)-Leu-Arg(Pbf)-OH (SEQ ID NO: 11) (Peptide derivative Ia)).

$^1$H NMR (400 MHz, DMSO-d$_6$) δ ppm: 0.7-0.9 (m, 24H); 1.19 (d, J=7.1 Hz, 3H); 1.33 (s, 9H); 1.3-1.8 (m, 32H); 1.84 (s, 3H); 2.00 (s, 6H); 2.42 (s, 6H); 2.48 (s, 6H); 2.4-2.6 (m, 1H); 2.6-2.8 (m, 1H); 2.96 (s, 4H); 3.02 (br. s, 4H); 3.60 (s, 3H); 4.1-4.4 (m, 7H); 4.56 (q, J=7.3 Hz, 1H); 6.39, 6.65 (br. s×2, 6H); 7.68 (d, J=7.8 Hz, 1H); 7.78 (d, J=8.4 Hz, 1H); 7.9-8.1 (m, 4H); 8.11 (d, J=7.5 Hz, 1H); 8.27 (d, J=8.0 Hz, 1H).

(2) Deprotection of C-Terminus of Peptide Derivative IIIa to Give Ac-Arg(Pbf)-Leu-Asp(Ot-Bu)-Leu-Arg(Pbf)-Leu-Ala-Leu-OH (SEQ ID NO: 13)

In a 500 mL reaction container were placed 7.93 g (5 mmol) of Ac-Arg(Pbf)-Leu-Asp(Ot-Bu)-Leu-Arg(Pbf)-Leu-Ala-Leu-OMe (SEQ ID NO:12) (Peptide derivative IIIa), tap water (71.4 mL) and t-BuOH (238 mL). To this, 25 mL of a 1 N sodium hydroxide aqueous solution (25 mmol) was added dropwise at room temperature. The mixture was stirred at room temperature overnight, and 1 N hydrochloric acid (79.3 mL) was added dropwise thereto. After evaporation of t-BuOH under reduced pressure, MTBE (123.1 mL), THF (79.3 mL) and ethyl acetate (23.8 mL) were added to the residue, and suction filtration was performed. Purification by silica gel column chromatography was performed to give 7.48 g of Ac-Arg(Pbf)-Leu-Asp(Ot-Bu)-Leu-Arg(Pbf)-Leu-Ala-Leu-OH (SEQ ID NO: 13) as a white powder (94% yield).

$^1$H NMR (400 MHz, DMSO-d$_6$) δ ppm: 0.7-0.9 (m, 24H); 1.19 (d, J=7.0 Hz, 3H); 1.33 (s, 9H); 1.3-1.7 (m, 32H); 1.84 (s, 3H); 2.00 (s, 6H); 2.42 (s, 6H); 2.48 (s, 6H); 2.4-2.6 (m, 1H); 2.6-2.8 (m, 1H); 2.96 (s, 4H); 2.9-3.1 (m, 4H); 4.1-4.4 (m, 7H); 4.55 (dd, J1=14.5 Hz, J2=7.9 Hz, 1H); 6.42, 6.79 (br. s×2, 6H); 7.68 (d, J=8.1 Hz, 1H); 7.80 (d, J=7.8 Hz, 1H); 7.8-8.1 (m, 5H); 8.27 (d, J=7.9 Hz, 1H).

(3) Synthesis of Peptide Derivative IVa:

```
                                           (SEQ ID NO: 14)
Ac-Arg(Pbf)-Leu-Asp(Ot-Bu)-Leu-Arg(Pbf)-Leu-Ala-

Leu-Arg(Pbf)-Leu-Asp(Ot-Bu)-Leu-Arg(Pbf)-NH₂
```

In a 100 mL reaction container were placed 1.00 g (0.791 mmol) of Cl⁻.H₂⁺-Arg(Pbf)-Leu-Asp(Ot-Bu)-Leu-Arg(Pbf)-NH₂ (SEQ ID NO: 25) (a hydrochloric acid salt of Peptide derivative Ib), 1.51 g (0.956 mmol) of Ac-Arg(Pbf)-Leu-Asp(Ot-Bu)-Leu-Arg(Pbf)-Leu-Ala-Leu-OH (SEQ ID NO:13), DMF (10 mL), 0.13 g (0.96 mmol) of HOBt, 0.30 g (1.6 mmol) of EDC.HCl and THF (18 mL). The mixture was cooled in an ice bath. While the mixture was stirred under cooling in the ice bath, 0.33 mL (2.4 mmol) of TEA was added. The mixture was stirred under cooling in the ice bath for one week. To this, 0.5 N hydrochloric acid (5 mL), tap water (15 mL) and MTBE (10 mL) were added, and the mixture was stirred at room temperature. After the mixture was left to stand, the resulting layers were separated. The organic layer was concentrated under reduced pressure and the residue was purified by silica gel column chromatography to give 1.28 g of Ac-Arg(Pbf)-Leu-Asp(Ot-Bu)-Leu-Arg(Pbf)-Leu-Ala-Leu-Arg(Pbf)-Leu-Asp(Ot-Bu)-Leu-Arg(Pbf)-NH₂ (SEQ ID NO: 14) (Peptide derivative IVa) as a white powder (58% yield from Cl⁻.H₂⁺-Arg(Pbf)-Leu-Asp(Ot-Bu)-Leu-Arg(Pbf)-NH₂ (SEQ ID NO: 25) (the hydrochloric acid salt of Peptide derivative Ib)).

$^1$H NMR (400 MHz, DMSO-d$_6$) δ ppm: 0.7-0.9 (m, 36H); 1.23 (d, J=7.2 Hz, 3H); 1.3-1.9 (m, 76H); 1.88 (s, 3H); 1.9-2.1 (m, 12H); 2.4-2.45 (m, 12H); 2.45-2.5 (m, 12H); 2.5-2.6 (m, 2H); 2.70 (dd, J1=17.9 Hz, J2=6.9 Hz, 2H); 2.9-3.0 (m, 8H); 3.02 (br. s, 8H); 4.0-4.3 (m, 11H); 4.4-4.6 (m, 2H); 6.43, 6.72 (br. s×2, 12H); 6.87 (s, 1H); 7.00 (br. s, 1H); 7.07 (br. s, 1H); 7.65 (t, J=7.4 Hz, 1H); 7.7-7.9 (m, 3H); 7.82 (d, J=6.8 Hz, 2H); 7.9-8.1 (m, 3H); 8.0-8.2 (m, 2H); 8.17 (d, J=7.2 Hz, 1H). MS (ESI) m/z: 1392.7 ([M+2H]$^{2+}$).

(4) Removal of Side-Chain Protecting Groups from Peptide Derivative IVa and Preparation of Disulfuric Acid Salt of Peptide Derivative Represented by General Formula (IX):

```
                                            (SEQ ID NO: 4)
Ac-Arg-Leu-Asp-Leu-Arg-Leu-Ala-Leu-Arg-Leu-Asp-

Leu-Arg-NH₂•2H₂SO₄
```

In a 500 mL reaction container was placed 7.19 g (2.58 mmol) of Ac-Arg(Pbf)-Leu-Asp(Ot-Bu)-Leu-Arg(Pbf)-Leu-Ala-Leu-Arg(Pbf)-Leu-Asp(Ot-Bu)-Leu-Arg(Pbf)-NH₂ (SEQ ID NO: 14) (Peptide derivative IVa). To this, 52 mL (0.67 mol) of TFA and tap water (2.7 mL) were added. The mixture was stirred at room temperature for 1.5 hours and concentrated under reduced pressure. While the residue (61.75 g) was stirred, MTBE (217 mL) was added to induce the precipitation of a solid. Suction filtration and vacuum drying were performed to give 4.71 g of Ac-Arg-Leu-Asp-Leu-Arg-Leu-Ala-Leu-Arg-Leu-Asp-Leu-Arg-NH₂.2H₂SO₄ (SEQ ID NO:4) as a whitish powder (98% yield).

$^1$H NMR (400 MHz, DMSO-d$_6$) δ ppm: 0.8-0.9 (m, 36H); 1.19 (d, J=6.8 Hz, 3H); 1.3-1.8 (34H); 1.87 (s, 3H); 2.4-2.6 (m, 2H); 2.6-2.8 (m, 2H); 3.09 (d, J=6.0 Hz, 8H); 4.1-4.4 (m, 11H); 4.5-4.6 (m, 2H), 6.5-8.3 (m, 31H).

Example 2

Preparation of Tetramethanesulfonic Acid Salt of Peptide Derivative Represented by General Formula (VII):

```
                                            (SEQ ID NO: 15)
Ac-Arg-Leu-Asp-Leu-Arg-Leu-Ala-Leu-Arg-Leu-Asp-

Leu-Arg-NH₂•4MsOH
```

In a 30 mL reaction container was placed 0.54 g (0.19 mmol) of Ac-Arg(Pbf)-Leu-Asp(Ot-Bu)-Leu-Arg(Pbf)-Leu-Ala-Leu-Arg(Pbf)-Leu-Asp(Ot-Bu)-Leu-Arg(Pbf)-NH₂ (SEQ ID NO: 14) (Peptide derivative IVa). To this, a mixture of 4.0 mL (52 mmol) of TFA, 0.10 mL (1.3 mmol) of MsOH and 0.20 mL (0.97 mmol) of triisopropylsilane was added. The mixture was stirred at room temperature for 2.1 hours and concentrated under reduced pressure. While the residue (2.76 g) was stirred, MTBE (14 mL) was added to induce the precipitation of a solid. Suction filtration and vacuum drying were performed to give 0.46 g of Ac-Arg-Leu-Asp-Leu-Arg-Leu-Ala-Leu-Arg-Leu-Asp-Leu-Arg-NH₂.4MsOH (SEQ ID NO:15) as a light yellow powder (quantitative yield).

$^1$H NMR (400 MHz, DMSO-d$_6$) δ ppm: 0.8-0.9 (m, 36H); 1.21 (d, J=6.8 Hz, 3H); 1.3-1.8 (34H); 1.88 (s, 3H); 2.38 (s, 12H); 2.4-2.6 (m, 2H); 2.7-2.8 (m, 2H); 3.09 (d, J=5.6 Hz, 8H); 4.1-4.6 (m, 13H); 4.5-4.6 (m, 2H), 6.6-8.3 (m, 31H).

Example 3

Preparation of Disulfuric Acid Salt of Peptide Derivative Represented by General Formula (X):

```
                                            (SEQ ID NO: 5)
Ac-Arg-Leu-Asp-Leu-Arg-Leu-Leu-Leu-Arg-Leu-Asp-

Leu-Arg-NH₂•2H₂SO₄
```

(1) Synthesis of Peptide Derivative IIIa (X=Leu):

```
                                            (SEQ ID NO: 16)
Ac-Arg(Pbf)-Leu-Asp(Ot-Bu)-Leu-Arg(Pbf)-Leu-Leu-

Leu-OMe
```

In a 100 mL reaction container were placed 1.14 g (2.79 mmol) of Cl⁻.H₂⁺-Leu-Leu-Leu-OMe (a hydrochloric acid salt of Peptide derivative IIa (X=Leu)) and 0.40 g (3.0 mmol) of HOBt, and they were suspended in THF (5 mL). To this suspension, 0.75 g (3.9 mmol) of EDC.HCl was added. While the mixture was cooled in an ice bath, 1.04 mL (9.46 mmol) of NMM was added dropwise. Separately, 2.92 g (2.29 mmol) of Ac-Arg(Pbf)-Leu-Asp(Ot-Bu)-Leu-Arg(Pbf)-OH (SEQ ID NO:11) (Peptide derivative Ia) was dissolved in a mixed solvent of DMF (8.2 mL) and THF (12.1 mL). This solution was added dropwise to the previously prepared reaction suspension cooled in the ice bath. The mixture was stirred for three days, allowing the temperature to rise to room temperature. To this, 0.5 N hydrochloric acid (19 mL) and THF (19 mL) were added. Suction filtration and drying were performed to give 2.10 g of Ac-Arg(Pbf)-Leu-Asp(Ot-Bu)-Leu-Arg(Pbf)-Leu-Leu-Leu-OMe (SEQ ID NO: 16) (Peptide derivative IIIa) as a light yellow powder (46% yield).

¹H NMR (400 MHz, DMSO-d₆) δ ppm: 0.8-1.0 (m, 30H); 1.37 (s, 9H); 1.44 (s, 12H); 1.2-1.8 (m, 23H); 1.88 (s, 3H); 2.04 (s, 6H); 2.46 (s, 6H); 2.57 (s, 6H); 2.4-2.6 (m, 1H); 2.71 (dd, J1=16.2 Hz, J2=6.2 Hz, 1H); 3.00 (s, 4H); 3.0-3.1 (m, 4H); 3.63 (s, 3H); 4.1-4.4 (m, 7H); 4.59 (dd, J1=14.4 Hz, J2=7.6 Hz, 1H); 6.42, 6.66 (br. s×2, 6H); 7.74 (d, J=8.4 Hz, 1H); 7.81 (d, J=8.0 Hz, 1H); 7.87 (d, J=8.8 Hz, 1H); 7.96 (d, J=7.6 Hz, 1H); 7.9-8.1 (m, 2H); 8.15 (d, J=7.6 Hz, 1H); 8.32 (d, J=8.0 Hz, 1H).

(2) Synthesis of Peptide Derivative IVa (X=Leu):

```
                                           (SEQ ID NO: 17)
Ac-Arg(Pbf)-Leu-Asp(Ot-Bu)-Leu-Arg(Pbf)-Leu-Leu-

Leu-Arg(Pbf)-Leu-Asp(Ot-Bu)-Leu-Arg(Pbf)-NH₂
```

In a 50 mL reaction container was placed a solution of 1.20 g (0.737 mmol) of Ac-Arg(Pbf)-Leu-Asp(Ot-Bu)-Leu-Arg(Pbf)-Leu-Leu-Leu-OMe (SEQ ID NO: 16) (Peptide derivative IIIa) in t-BuOH (10.3 mL). To this, tap water (8.5 mL) was added. While the mixture was cooled in an ice bath, a solution of 45.76 mg (1.090 mmol) of lithium hydroxide monohydrate in tap water (2.8 mL) was added. The mixture was stirred under cooling in the ice bath for one week. The supernatant was discarded by decantation. After addition of tap water (14.3 mL), 1 N hydrochloric acid (1.1 mL) and t-BuOH (3 mL), suction filtration and drying were performed to produce Ac-Arg(Pbf)-Leu-Asp(Ot-Bu)-Leu-Arg(Pbf)-Leu-Leu-Leu-OH (SEQ ID NO: 28) as a white powder. The obtained peptide derivative was placed in a 50 mL reaction container, and to this were added 0.93 g (0.73 mmol) of Cl⁻.H₂⁺-Arg(Pbf)-Leu-Asp(Ot-Bu)-Leu-Arg(Pbf)-NH₂ (SEQ ID NO: 25) (a hydrochloric acid salt of Peptide derivative Ib), DMF (8.3 mL), 97.82 mg (0.7239 mmol) of HOBt, 0.36 g (1.9 mmol) of EDC.HCl and THF (14.5 mL). The mixture was cooled in the ice bath. While the mixture was stirred under cooling in the ice bath, 0.37 mL (2.7 mmol) of TEA was added. The mixture was stirred under cooling in the ice bath overnight. To this, 0.5 N hydrochloric acid (3.6 mL), tap water (10 mL) and MTBE (7.2 mL) were added, and the mixture was stirred at room temperature and then left to stand. The resulting layers were separated. The organic layer was concentrated under reduced pressure and the residue was purified by silica gel column chromatography to give 0.65 g of Ac-Arg(Pbf)-Leu-Asp(Ot-Bu)-Leu-Arg(Pbf)-Leu-Leu-Leu-Arg(Pbf)-Leu-Asp(Ot-Bu)-Leu-Arg(Pbf)-NH₂ (SEQ ID NO: 17) (Peptide derivative IVa) as a whitish amorphous solid (31% two-step yield from Ac-Arg(Pbf)-Leu-Asp(Ot-Bu)-Leu-Arg(Pbf)-Leu-Leu-Leu-OMe (SEQ ID NO: 16) (Peptide derivative IIIa)).

¹H NMR (400 MHz, DMSO-d₆) δ ppm: 0.7-0.9 (m, 42H); 1.3-1.8 (m, 73H); 1.88 (s, 3H); 1.9-2.1 (m, 12H); 2.4-2.5 (m, 24H); 2.6-2.8 (m, 4H); 2.9-3.0 (m, 8H); 2.9-3.1 (br. s, 8H); 4.0-4.8 (m, 13H); 6.40, 6.63 (br. s×2, 12H); 7.0-8.4 (m, 15H).

(3) Preparation of Disulfuric Acid Salt of Peptide Derivative:

```
                                           (SEQ ID NO: 5)
Ac-Arg-Leu-Asp-Leu-Arg-Leu-Leu-Leu-Arg-Leu-Asp-

Leu-Arg-NH₂•2H₂SO₄
```

In a 50 mL reaction container was placed 0.78 g (0.28 mmol) of Ac-Arg(Pbf)-Leu-Asp(Ot-Bu)-Leu-Arg(Pbf)-Leu-Leu-Leu-Arg(Pbf)-Leu-Asp(Ot-Bu)-Leu-Arg(Pbf)-NH₂ (SEQ ID NO: 17) (Peptide derivative IVa). To this, 5.7 mL (74 mmol) of TFA and tap water (0.29 mL) were added. The mixture was stirred at room temperature for 1.9 hours. MTBE (15 mL) was added to induce the precipitation of a solid. After 1.5-hour stirring at room temperature, suction filtration was performed to give 0.45 g of Ac-Arg-Leu-Asp-Leu-Arg-Leu-Leu-Leu-Arg-Leu-Asp-Leu-Arg-NH₂.2H₂SO₄ (SEQ ID NO: 5) as a whitish powder (86% yield).

¹H NMR (400 MHz, DMSO-d₆) δ ppm: 0.8-1.0 (m, 42H); 1.3-1.8 (37H); 1.90 (s, 3H); 2.4-2.6 (m, 2H); 2.7-2.9 (m, 2H); 3.1-3.2 (br. s, 8H); 4.1-4.4 (m, 11H); 4.5-4.6 (m, 2H), 6.6-8.4 (m, 31H).

Example 4

Preparation of Disulfuric Acid Salt of Peptide Derivative Represented by General Formula (IX):

```
                                            (SEQ ID NO: 4)
Ac-Arg-Leu-Asp-Leu-Arg-Leu-Ala-Leu-Arg-Leu-Asp-

Leu-Arg-NH₂•2H₂SO₄
```

(1) Synthesis of Peptide Derivative IVb:

```
                                           (SEQ ID NO: 18)
Ac-Arg(Pbf)-Leu-Asp(Ot-Bu)-Leu-Arg(Pbf)-Leu-Ala-

Leu-Arg(Pbf)-Leu-Asp(Ot-Bu)-Leu-Arg(Pbf)-OMe
```

In a 200 mL reaction container were placed 2.50 g (1.9 mmol) of Cl⁻.H₂⁺-Arg(Pbf)-Leu-Asp(Ot-Bu)-Leu-Arg(Pbf)-OMe (SEQ ID NO: 19) (a hydrochloric acid salt of Peptide derivative Ic) and 341 mg (2.52 mmol) of HOBt, and they were suspended in THF (19.9 mL). The suspension was cooled in an ice bath. To this, 1.42 g (6.48 mmol) of EDC.HCl was added, and then 1.39 mL (12.6 mmol) of NMM was added dropwise. Separately, 2.83 g (1.8 mmol) of Ac-Arg(Pbf)-Leu-Asp(Ot-Bu)-Leu-Arg(Pbf)-Leu-Ala-Leu-OH (SEQ ID NO: 13) was dissolved in a mixed solvent of DMF (19.8 mL) and THF (19.8 mL). This solution was added dropwise to the previously prepared reaction suspension cooled in the ice bath. The mixture was stirred under cooling in the ice bath for three days. To this, 0.5 N hydrochloric acid (56.6 mL) and ethyl acetate (28.3 mL) were added, and the resulting layers were separated. The organic layer was concentrated under reduced pressure and the residue was purified by silica gel column chromatography to give 2.81 g of Ac-Arg(Pbf)-Leu-Asp(Ot-Bu)-Leu-Arg(Pbf)-Leu-Ala-Leu-Arg (Pbf)-Leu-Asp(Ot-Bu)-Leu-Arg(Pbf)-OMe (SEQ ID NO: 18) (Peptide derivative IVb) as a white solid (56% yield from Ac-Arg(Pbf)-Leu-Asp(Ot-Bu)-Leu-Arg(Pbf)-Leu-Ala-Leu-OH (SEQ ID NO: 13)).

¹H NMR (400 MHz, DMSO-d₆) δ ppm: 0.81-0.94 (m, 36H), 1.20 (d, J=6.8 Hz, 3H), 1.2-1.6 (76H); 1.85 (s, 3H); 2.00 (s, 12H); 2.42 (s, 12H); 2.47 (s, 12H); 2.5-2.7 (m, 4H); 2.95 (s, 8H), 3.01 (br, 8H); 3.58 (s, 3H); 4.1-4.4 (m, 11H); 4.52 (m, 2H).

(2) Removal of Side-Chain Protecting Groups from Peptide Derivative IVb to Give Ac-Arg-Leu-Asp-Leu-Arg-Leu-Ala-Leu-Arg-Leu-Asp-Leu-Arg-OMe.2H₂SO₄ (SEQ ID NO: 20)

In a 50 mL reaction container was placed 2.80 g (1.0 mmol) of Ac-Arg(Pbf)-Leu-Asp(Ot-Bu)-Leu-Arg(Pbf)-Leu-Ala-Leu-Arg(Pbf)-Leu-Asp(Ot-Bu)-Leu-Arg(Pbf)-OMe (SEQ ID NO: 18) (Peptide derivative IVb). While the peptide derivative was cooled in water, 40 mL (0.52 mol) of TFA and tap water (2 mL) were added. The mixture was stirred at room temperature for 1 hour and concentrated by an evaporator. To the concentrated residue was added MTBE (91 mL), and the mixture was stirred at room temperature overnight. Suction filtration and vacuum drying were performed to give 2.16 g of Ac-Arg-Leu-Asp-Leu-Arg-Leu-Ala-Leu-Arg-Leu-Asp-Leu-Arg-OMe.2H$_2$SO$_4$ (SEQ ID NO: 20) as a white solid (quantitative yield).

$^1$H NMR (400 MHz, DMSO-d$_6$) δ ppm: 0.7-0.9 (m, 36H), 1.20 (d, J=5.0 Hz, 3H); 1.3-1.7 (m, 34H); 1.88 (s, 3H); 2.4-2.7 (m, 4H); 3.10 (d, J=5.6 Hz, 8H), 3.61 (s, 3H); 4.2-4.3 (m, 11H); 4.53 (m, 2H).

(3) Amidation of C-Terminus to Give Ac-Arg-Leu-Asp-Leu-Arg-Leu-Ala-Leu-Arg-Leu-Asp-Leu-Arg-NH$_2$.2H$_2$SO$_4$ (SEQ ID NO:4)

In a 50 mL reaction container was placed 2.13 g (1.1 mmol) of Ac-Arg-Leu-Asp-Leu-Arg-Leu-Ala-Leu-Arg-Leu-Asp-Leu-Arg-OMe.2H$_2$SO$_4$ (SEQ ID NO: 20). While the peptide derivative was cooled in water, 42.6 mL of an 8 N ammonia/MeOH solution (341 mmol) was added. The mixture was stirred at room temperature for one week. Suction filtration was performed and the resulting cake was washed twice with MeOH (8.5 mL) and once with MTBE (8.5 mL). Vacuum drying was performed to give 2.07 g of Ac-Arg-Leu-Asp-Leu-Arg-Leu-Ala-Leu-Arg-Leu-Asp-Leu-Arg-NH$_2$.2H$_2$SO$_4$ (SEQ ID NO:4) as a white solid (quantitative yield).

Example 5

Salt Exchange Reaction to Prepare Tetrahydrochloric Acid Salt of Peptide Derivative:

(SEQ ID NO: 9)
Ac-Arg-Leu-Asp-Leu-Arg-Leu-Ala-Leu-Arg-Leu-Asp-

Leu-Arg-NH$_2$•4HCl

In a 500 mL reaction container was placed 4.71 g (2.54 mmol) of Ac-Arg-Leu-Asp-Leu-Arg-Leu-Ala-Leu-Arg-Leu-Asp-Leu-Arg-NH$_2$.2H$_2$SO$_4$ (SEQ ID NO: 4). To this, 180 mL of 0.5 N hydrochloric acid (90 mmol) and THF (300 mL) were added. The mixture was stirred at room temperature for 15 hours and the supernatant (370 mL) was discarded. After addition of THF (360 mL), the mixture was stirred and then left to stand, and the supernatant was discarded. After addition of THF (100 mL) and MTBE (263 mL), the mixture was stirred at room temperature for 0.4 hours. Suction filtration and vacuum drying were performed to give 3.15 g of Ac-Arg-Leu-Asp-Leu-Arg-Leu-Ala-Leu-Arg-Leu-Asp-Leu-Arg-NH$_2$.4HCl (SEQ ID NO: 9) as a white powder (69% yield).

IR (KBr) ν cm$^{-1}$: 3273 (s); 2957 (m); 1626 (s); 1541 (s).

Example 6

Salt Exchange Reaction to Prepare Tetrahydrochloric Acid Salt of Peptide Derivative:
Ac-Arg-Leu-Asp-Leu-Arg-Leu-Leu-Leu-Arg-Leu-Asp-Leu-Arg-NH$_2$.4HCl (SEQ ID NO: 10)

In a 50 mL reaction container was placed 0.41 g (0.22 mmol) of Ac-Arg-Leu-Asp-Leu-Arg-Leu-Leu-Leu-Arg-Leu-Asp-Leu-Arg-NH$_2$.2H$_2$SO$_4$ (SEQ ID NO:5). To this, 15 mL of 0.5 N hydrochloric acid (7.5 mmol) and THF (10 mL) were added. The mixture was stirred at room temperature for 19 hours and the supernatant (32 mL) was discarded. After addition of THF (45 mL), the mixture was stirred and then left to stand, and the supernatant was discarded. After addition of MTBE (8 mL), the mixture was stirred at room temperature for 0.5 hours. Suction filtration and vacuum drying were performed to give 0.11 g of Ac-Arg-Leu-Asp-Leu-Arg-Leu-Leu-Leu-Arg-Leu-Asp-Leu-Arg-NH$_2$.4HCl (SEQ ID NO: 10) as a white powder (28% yield).

$^1$H NMR (400 MHz, DMSO-d$_6$) δ ppm: 0.8-1.0 (m, 42H); 1.3-1.8 (37H); 1.89 (s, 3H); 2.4-2.6 (m, 2H); 2.75 (dd, J1=16.6 Hz, J2=5.8 Hz, 2H); 3.0-3.1 (m, 8H); 4.1-4.4 (m, 11H); 4.4-4.6 (m, 2H), 6.6-8.4 (m, 31H).

Example 7

Salt Exchange Reaction to Prepare Tetrahydrochloric Acid Salt of Peptide Derivative:

(SEQ ID NO: 9)
Ac-Arg-Leu-Asp-Leu-Arg-Leu-Ala-Leu-Arg-Leu-Asp-

Leu-Arg-NH$_2$•4HCl

In a 10 mL reaction container was placed 0.17 g (0.083 mmol) of Ac-Arg-Leu-Asp-Leu-Arg-Leu-Ala-Leu-Arg-Leu-Asp-Leu-Arg-NH$_2$.4MsOH (SEQ ID NO:15). To this, 6.9 mL of 0.5 N hydrochloric acid (3.5 mmol) and THF (4.6 mL) were added. The mixture was stirred at room temperature overnight and the supernatant was discarded. After addition of THF (15 mL), the mixture was stirred and then left to stand, and the supernatant was discarded. After addition of MTBE (5 mL), the mixture was stirred at room temperature for 1.1 hours. Suction filtration and vacuum drying were performed to give 0.06 g of Ac-Arg-Leu-Asp-Leu-Arg-Leu-Ala-Leu-Arg-Leu-Asp-Leu-Arg-NH$_2$.4HCl (SEQ ID NO: 9) as a white solid (40% yield).

Example 8

Salt Exchange Reaction to Prepare Tetrahydrochloric Acid Salt of Peptide Derivative:

(SEQ ID NO: 9)
Ac-Arg-Leu-Asp-Leu-Arg-Leu-Ala-Leu-Arg-Leu-Asp-

Leu-Arg-NH$_2$•4HCl

In a 50 mL reaction container was placed 0.18 g (0.085 mmol) of Ac-Arg-Leu-Asp-Leu-Arg-Leu-Ala-Leu-Arg-Leu-Asp-Leu-Arg-NH$_2$.4TFA (SEQ ID NO:21). To this, 12.4 mL of 0.3 N hydrochloric acid (3.72 mmol) and THF (12 mL) were added. The mixture was agitated at room temperature. The mixture was centrifuged to obtain sediment and the supernatant was discarded. After addition of THF (9 mL), the mixture was agitated and then left to stand, and the supernatant was discarded. After addition of MTBE (4 mL), the mixture was agitated. Suction filtration and vacuum drying were performed to give 0.07 g of Ac-Arg-Leu-Asp-Leu-Arg-Leu-Ala-Leu-Arg-Leu-Asp-Leu-Arg-NH$_2$.4HCl (SEQ ID NO: 9) as a white solid (46% yield).

Example 9

Synthesis of Peptide Derivative Ia
(1) Coupling of Peptide Derivative Vb (N-Terminal Protecting Group: Fmoc Group) with Peptide Derivative VIa to Give Fmoc-Arg(Pbf)-Leu-Asp(Ot-Bu)-Leu-Arg(Pbf)-OMe (SEQ ID NO: 22)

In a 200 mL reaction container were placed 8.26 g (10.9 mmol) of Cl⁻.H₂⁺-Asp(Ot-Bu)-Leu-Arg(Pbf)-OMe (a hydrochloric acid salt of Peptide derivative VIa) and 1.47 g (10.9 mmol) of HOBt, and they were suspended in THF (84.6 mL). The suspension was cooled in an ice bath, and 2.40 g (12.5 mmol) of EDC.HCl was added thereto. While the mixture was cooled in the ice bath, a solution of 8.52 g (10.9 mmol) of Fmoc-Arg(Pbf)-Leu-OH (Peptide derivative Vb (N-terminal protecting group: Fmoc group)) in THF (9.2 mL) was added dropwise, and a solution of 2.75 g (27.2 mmol) of NMM in THF (33 mL) was then added dropwise. The mixture was stirred under cooling in the ice bath overnight. To this, ethyl acetate (59.2 mL) and tap water (42.3 mL) were added, and the resulting layers were separated. The organic layer was washed successively with a 5% sodium bicarbonate solution (50.8 mL), 1 N hydrochloric acid (50.8 mL) and tap water (50.8 mL). The organic layer was concentrated under reduced pressure by an evaporator and the residue was dried with a vacuum pump to give 20.54 g of Fmoc-Arg(Pbf)-Leu-Asp(Ot-Bu)-Leu-Arg(Pbf)-OMe (SEQ ID NO:22) as a white solid (quantitative yield).

$^1$H NMR (400 MHz, CDCl₃) δ ppm: 0.84 (d, J=6.2 Hz, 6H); 0.88 (d, J=6.2 Hz, 6H); 1.3-2.0 (m, 35H); 2.07 (s, 6H); 2.49 (s, 3H); 2.51 (s, 3H); 2.56 (s, 3H); 2.59 (s, 3H); 2.84 (dd, J1=15.1 Hz, J2=4.2 Hz, 2H); 2.91 (s, 4H); 3.1-3.3 (br. s, 2H); 3.32 (br. s, 2H); 3.71 (s, 3H); 4.0-4.2 (m, 2H); 4.2-4.4 (m, 3H); 4.4-4.6 (m, 1H); 4.5-4.7 (m, 2H); 6.14, 6.37 (br. s×2, 6H); 6.66 (br. s, 1H); 7.1-7.3 (m, 1H); 7.21 (d, J=7.8 Hz, 2H); 7.36 (t, J=7.4 Hz, 2H); 7.5-7.6 (br. s, 2H); 7.60 (t, J=6.7 Hz, 2H); 7.6-7.8 (br. s, 1H); 7.73 (d, J=7.6 Hz, 2H).

(2) Deprotection of N-terminus to give Cl⁻.H₂⁺-Arg(Pbf)-Leu-Asp(Ot-Bu)-Leu-Arg(Pbf)-OMe (SEQ ID NO: 19)

In a 200 mL reaction container were placed 14.68 g (10 mmol) of Fmoc-Arg(Pbf)-Leu-Asp(Ot-Bu)-Leu-Arg(Pbf)-OMe (SEQ ID NO: 22) and THF (95.4 mL). To this, 1.53 g (18 mmol, 1.8 eq.) of piperidine was added dropwise at room temperature. The reaction solution was stirred at room temperature for 7 hours. To this, MTBE (58.7 mL), AcOEt (14.7 mL) and 0.5 N hydrochloric acid (88 mL) were added. The organic layer was separated and washed successively with 1 N hydrochloric acid (88 mL) and tap water (88 mL). The organic layer was concentrated by an evaporator. To the residue were added MeOH (58.7 mL), tap water (29.4 mL), MTBE (58.7 mL) and n-heptane (58.7 mL) so that the residue was dissolved. The resulting layers were separated. The lower layer was washed twice with a mixed solution of MTBE/heptane (1/1 (v/v)) (117.4 mL). MeOH was evaporated off under reduced pressure. To the residue were added tap water (29.4 mL), ethyl acetate (58.7 mL) and sodium chloride (2.0 g), and the resulting layers were separated. The organic layer was concentrated under reduced pressure to give 12.66 g of Cl⁻.H₂⁺-Arg(Pbf)-Leu-Asp(Ot-Bu)-Leu-Arg(Pbf)-OMe (SEQ ID NO:19) as a white solid (98% yield).

$^1$H NMR (400 MHz, CDCl₃) δ ppm: 0.84 (m, 12H); 1.38 (s, 9H); 1.45 (s, 12H); 1.6-2.4 (m, 14H); 2.07 (s, 6H); 2.47 (s, 6H); 2.54 (s, 6H); 2.7-2.9 (m, 2H); 2.94 (s, 4H); 3.1-3.4 (m, 4H); 3.68 (s, 3H); 4.0-4.7 (m, 5H); 6.50 (br. s, 6H); 7.6-9.4 (m, 8H).

(3) Acetylation of N-Terminus to Give Ac-Arg(Pbf)-Leu-Asp(Ot-Bu)-Leu-Arg(Pbf)-OMe (SEQ ID NO: 23)

In a 100 mL reaction container were placed 8.97 g (7 mmol) of Cl⁻.H₂⁺-Arg(Pbf)-Leu-Asp(Ot-Bu)-Leu-Arg(Pbf)-OMe (SEQ ID NO: 19) and THF (63 mL). The mixture was cooled in the ice bath. While the mixture was cooled in the ice bath, 1.07 g (10.5 mmol, 1.5 eq.) of acetic anhydride was added. While the mixture was cooled in the ice bath, 1.77 g (17.5 mmol, 2.5 eq.) of TEA was added dropwise. The mixture was stirred under cooling in the ice bath for 2 hours, and ethyl acetate (36 mL) and 1 N hydrochloric acid (36 mL) were added. The organic layer was separated and washed successively with 1 N hydrochloric acid (36 mL) and a 5% sodium bicarbonate solution (36 mL). The organic layer was concentrated under reduced pressure to give 8.46 g of Ac-Arg(Pbf)-Leu-Asp(Ot-Bu)-Leu-Arg(Pbf)-OMe (SEQ ID NO: 23) as a white solid (93% yield).

$^1$H NMR (400 MHz, CDCl₃) δ ppm: 0.85 (d, J=6.6 Hz, 3H); 0.88 (d, J=6.4 Hz, 6H); 0.93 (d, 5.4 Hz, 3H); 1.42 (s, 9H); 1.46 (s, 12H); 1.3-2.0 (m, 14H); 2.05 (s, 3H); 2.09 (s, 6H); 2.48 (s, 3H); 2.50 (s, 3H); 2.55 (s, 3H); 2.57 (s, 3H); 2.7-2.8 (m, 1H); 2.9-3.1 (m, 1H); 2.95 (s, 4H); 3.1-3.3 (m, 3H); 3.3-3.4 (m, 1H); 3.72 (s, 3H); 3.9-4.1 (m, 1H); 4.4-4.6 (m, 2H); 4.5-4.7 (m, 2H); 6.0-6.5 (m, 6H); 7.14 (d, J=8.7 Hz, 1H); 7.4-7.5 (m, 1H); 7.5-7.7 (m, 3H).

(4) Deprotection of C-Terminus to Give Peptide Derivative Ia:

(SEQ ID NO: 11)
Ac-Arg(Pbf)-Leu-Asp(Ot-Bu)-Leu-Arg(Pbf)-OH

In a 500 mL reaction container were placed 8.11 g (6.3 mmol) of Ac-Arg(Pbf)-Leu-Asp(Ot-Bu)-Leu-Arg(Pbf)-OMe (SEQ ID NO: 23), t-BuOH (243.5 mL) and tap water (73.1 mL) so that the peptide derivative was dissolved. While the mixture was cooled in a water bath, 9.45 mL of a 1 N sodium hydroxide aqueous solution (9.45 mmol, 1.5 eq.) was added dropwise. While the mixture was stirred under cooling in an ice bath overnight, 10.4 mL of 1 N hydrochloric acid (10.4 mmol; 1.65 eq.) was added dropwise. The reaction solution was concentrated under reduced pressure, and ethyl acetate (105.5 mL) and tap water (40.6 mL) were added thereto. The resulting layers were separated. The organic layer was washed successively with a 0.5% KHCO₃ aqueous solution (81.2 mL), a 0.25% KHCO₃ aqueous solution (81.2 mL) and 0.2 N hydrochloric acid (81.2 mL). The organic layer was concentrated under reduced pressure to give 7.68 g of Ac-Arg(Pbf)-Leu-Asp(Ot-Bu)-Leu-Arg(Pbf)-OH (SEQ ID NO:11) (Peptide derivative Ia) as a white solid (95.6% yield).

$^1$H NMR (400 MHz, DMSO-d₆) δ ppm: 0.82 (d, J=6.4 Hz, 6H); 0.85 (d, J=6.6 Hz, 6H); 1.33 (s, 9H); 1.41 (s, 12H); 1.3-1.5 (m, 8H); 1.5-1.7 (m, 5H); 1.6-1.9 (m, 1H); 1.84 (s, 3H); 2.00 (s, 6H); 2.42 (s, 6H); 2.48 (s, 6H); 2.4-2.6 (m, 1H); 2.68 (dd, J1=15.8 Hz, J2=6.2 Hz, 1H); 2.96 (m, 4H); 2.9-3.1 (m, 4H); 4.09 (dd, J1=13.1 Hz, J2=7.6 Hz, 1H); 4.1-4.4 (m, 3H); 4.55 (dd, J1=14.6 Hz, J2=7.7 Hz, 1H); 6.39, 6.5-6.9 (br. s×2, 6H); 7.63 (d, J=8.5 Hz, 1H); 7.91 (d, J=8.0 Hz, 1H); 7.98 (d, J=7.7 Hz, 1H); 8.06 (d, J=7.4 Hz, 1H); 8.26 (m, 1H).

Example 10

Synthesis of Peptide Derivative Ib
(1) Coupling of Peptide Derivative Vb (N-Terminal Protecting Group: Fmoc) with Peptide Derivative VIb to Give (SEQ ID NO: 24)
Fmoc-Arg(Pbf)-Leu-Asp(Ot-Bu)-Leu-Arg(Pbf)-NH₂

In a 100 mL reaction container were placed 1.00 g (1.41 mmol) of Cl⁻.H₂⁺-Asp(Ot-Bu)-Leu-Arg(Pbf)-NH₂ (a hydrochloric acid salt of Peptide derivative VIb), DMF (2.1 mL), THF (1.5 mL), 0.20 g (1.5 mmol) of HOBt, 0.32 g (1.7 mmol) of EDC.HCl and 0.24 mL (1.7 mmol) of TEA. The mixture was cooled in an ice bath. While the mixture was cooled in the ice bath, a solution of 1.04 g (1.32 mmol) of Fmoc-Arg(Pbf)-Leu-OH (Peptide derivative Vb (N-terminal protecting group: Fmoc group)) in THF (3 mL) was added. The mixture was stirred under cooling in the ice bath overnight. MTBE (15 mL) and tap water (15 mL) were added to induce the precipitation of a solid. Suction filtration and drying were performed to give 1.77 g of Fmoc-Arg(Pbf)-Leu-Asp(Ot-Bu)-Leu-Arg(Pbf)-$NH_2$ (SEQ ID NO: 24) as a whitish powder (86% yield from Fmoc-Arg(Pbf)-Leu-OH (Peptide derivative Vb (N-terminal protecting group: Fmoc group)).

$^1$H NMR (400 MHz, DMSO-$d_6$) δ ppm: 0.7-0.9 (m, 12H); 1.32 (s, 9H); 1.3-1.8 (m, 26H); 2.00 (s, 3H); 2.00 (s, 3H); 2.42 (s, 6H); 2.5 (s, 6H); 2.5-2.6 (m, 1H); 2.6-2.7 (m, 1H); 2.94 (s, 2H); 2.95 (s, 2H); 3.0-3.1 (m, 4H); 4.00 (m, 1H); 4.13 (dd, J1=13.6 Hz, J2=8.0 Hz, 1H); 4.2-4.4 (m, 5H); 4.4-4.6 (m, 1H); 4.58 (dd, J1=14.6 Hz, J2=7.8 Hz, 1H) 6.42, 6.68 (br. s×2, 6H); 6.99 (s, 1H); 7.16 (s, 3H); 7.31 (t, J=7.5 Hz, 2H); 7.41 (t, J=7.5 Hz, 2H); 7.46 (d, J=8.4 Hz, 1H); 7.7-7.8 (m, 4H); 7.8-7.9 (m, 1H); 7.88 (d, J=7.6 Hz, 2H); 8.31 (d, J=7.6 Hz, 1H).

(2) Deprotection of N-Terminus to Give Hydrochloric Acid Salt of Peptide Derivative Ib:

```
                                                    (SEQ ID NO: 25)
Cl⁻•H₂⁺-Arg(Pbf)-Leu-Asp(Ot-Bu)-Leu-Arg(Pbf)-NH₂
```

In a 30 mL reaction container, DMF (2.5 mL) was added to 0.97 g (0.67 mmol) of Fmoc-Arg(Pbf)-Leu-Asp(Ot-Bu)-Leu-Arg(Pbf)-$NH_2$ (SEQ ID NOL 24) to produce a solution. To the solution, 0.10 mL (1.0 mmol) of piperidine was added, and the mixture was stirred at room temperature for 2.1 hours. MTBE (3 mL), ethyl acetate (7 mL) and 0.24 N hydrochloric acid (8.5 mL) were added to induce the precipitation of a solid. After overnight stirring at room temperature, suction filtration and drying were performed to give 0.77 g of Cl⁻.$H_2^+$-Arg(Pbf)-Leu-Asp(Ot-Bu)-Leu-Arg(Pbf)-$NH_2$ (SEQ ID NO: 25) (a hydrochloric acid salt of Peptide derivative Ib) as a light yellow powder (91.2% yield).

$^1$H NMR (400 MHz, $CDCl_3$) δ ppm: 0.82 (d, J=6.4 Hz, 3H); 0.8-0.9 (m, 9H); 1.33 (s, 9H); 1.3-1.6 (m, 10H); 1.41 (s, 12H); 1.6-1.8 (m, 4H); 2.01 (s, 3H); 2.01 (s, 3H); 2.42 (s, 3H); 2.43 (s, 3H); 2.48 (s, 6H); 2.4-2.6 (m, 1H); 2.6-2.8 (m, 1H); 2.96 (s, 4H); 3.0-3.1 (m, 4H); 3.79 (br. s, 1H); 4.14 (dd, J1=13.6 Hz, J2=8.0 Hz, 1H); 4.26 (dd, J1=14.8 Hz, J2=7.6 Hz, 1H); 4.3-4.5 (m, 1H); 4.61 (dd, J1=14.4 Hz, J2=8.0 Hz, 1H); 6.51, 6.86 (br. s×2, 6H); 7.00 (s, 1H); 7.21 (s, 1H) 7.3-8.2 (m, 5H); 8.47 (d, J=8.0 Hz, 1H); 8.55 (d, J=8.0 Hz, 1H).

Reference Example 1

Synthesis of Peptide derivative Vb:

```
Fmoc-Arg(Pbf)-Leu
```

(1) Preparation of Fmoc-Arg(Pbf)-Leu-Ot-Bu

In a 200 mL reaction container were placed 5.60 g (8.0 mmol) of Fmoc-Arg(Pbf)-OH.0.5IPE, 1.88 g (8.4 mmol) of Cl⁻.$H_2^+$-Leu-Ot-Bu and 1.08 g (8.0 mmol) of HOBt, and they were suspended in THF (39.2 mL). The suspension was cooled in an ice bath, and 1.69 g (8.8 mmol) of EDC.HCl was added thereto. The mixture was stirred under cooling in the ice bath for 30 minutes. To this, a solution of 1.78 g (17.6 mmol) of NMM in THF (5.6 mL) was added dropwise. The mixture was stirred under cooling in the ice bath for 4 hours. Ethyl acetate (14 mL) and 9% saline (28 mL) were added, and the resulting layers were separated. The organic layer was washed successively with a saturated sodium bicarbonate solution (28 mL), a 5% sodium bicarbonate solution (28 mL), 0.5 N hydrochloric acid (28 mL), 0.1 N hydrochloric acid (28 mL) and tap water (28 mL). The organic layer was concentrated under reduced pressure by an evaporator and the residue was dried with a vacuum pump to give 6.66 g of Fmoc-Arg(Pbf)-Leu-Ot-Bu as a white solid (quantitative yield).

$^1$H NMR (400 MHz, $CDCl_3$) δ ppm: 0.85 (d, J=6.8 Hz, 6H); 1.42 (m, 15H); 1.54-1.97 (m, 7H); 2.07 (s, 3H); 2.51 (s, 3H); 2.59 (s, 3H); 2.91 (s, 2H); 3.31 (br. s, 2H); 4.14 (m, 1H); 4.31-4.38 (m, 4H); 5.95-6.30 (br. s, 3H); 7.23 (m, 2H); 7.33 (t, J=7.5 Hz, 2H); 7.56 (d, J=7.4 Hz, 2H); 7.72 (d, J=7.6 Hz, 2H).

(2) Deprotection of C-Terminus to Give Peptide Derivative Vb (N-Terminal Protecting Group: Fmoc Group):

```
Fmoc-Arg(Pbf)-Leu-OH
```

In a 100 mL reaction container was placed 5.01 g (6.0 mmol) of Fmoc-Arg(Pbf)-Leu-Ot-Bu. To this, tap water (3 mL) and concentrated hydrochloric acid (3 mL) were added. The mixture was heated in an oil bath at 80° C. with stirring. Ethyl acetate (20 mL) and tap water (20 mL) were added and the resulting layers were separated. The organic layer was concentrated under reduced pressure and the residue was purified by silica gel column chromatography to give 4.79 g of Fmoc-Arg(Pbf)-Leu-OH (Peptide derivative Vb (N-terminal protecting group: Fmoc group)) as a white solid (quantitative yield).

$^1$H NMR (400 MHz, $CDCl_3$) δ ppm: 0.87 (d, J=4.9 Hz, 6H); 1.42 (s, 6H); 1.54-1.97 (m, 7H); 2.05 (s, 3H); 2.47 (s, 3H); 2.55 (s, 3H); 2.90 (s, 2H); 3.14-3.31 (br. s, 2H); 4.1-4.5 (m, 5H); 6.0-6.6 (br. s, 3H); 7.22 (m, 2H); 7.34 (t, J=7.4 Hz, 2H); 7.54 (d, J=7.4 Hz, 2H); 7.71 (d, J=7.6 Hz, 2H).

Reference Example 2

Synthesis of Peptide Derivative VIa:

```
Asp(Ot-Bu)-Leu-Arg(Pbf)-OMe
```

(1) Preparation of H-Arg(Pbf)-OMe

In a 30 mL reaction container, 6.73 g of a 5.2% HCl/MeOH solution (9.6 mmol) was added to 2.11 g (4.0 mmol) of Boc-Arg(Pbf)-OH. The reaction solution was stirred at room temperature overnight and was further stirred at an internal temperature of 39 to 42° C. for 5 hours. The reaction solution was concentrated by an evaporator and the residue was dried with a vacuum pump. To the dried concentrate, MTBE (10 mL) and tap water (10 mL) were added so that the concentrate was dissolved, and the resulting layers were separated. The aqueous layer was washed with MTBE (10 mL). To the aqueous layer were added 594 mg (5.6 mmol, 1.4 eq.) of sodium carbonate and ethyl acetate (40 mL), and the resulting layers were separated. The organic layer was washed three times with a 10% potassium carbonate aqueous solution (10 mL). The organic layer was concentrated. The precipitated white solid was filtered off using a cotton plug. The filtrate was concentrated to give 1.53 g of H-Arg(Pbf)-OMe as a pale yellow viscous oil (71% yield).

$^1$H NMR (400 MHz, CDCl$_3$) δ ppm: 1.46 (s, 6H); 1.62-1.85 (m, 4H); 2.09 (s. 3H); 2.53 (s, 3H); 2.58 (s, 3H); 2.95 (s, 2H); 3.19 (m, 2H); 3.50 (m, 1H); 3.83 (s, 3H); 6.0-6.15 (m, 3H).

(2) Preparation of Boc-Leu-Arg(Pbf)-OMe

In a 100 mL reaction container, 0.96 g (2.17 mmol) of H-Arg(Pbf)-OMe, 0.30 g (2.2 mmol, 1.02 eq.) of HOBt, 0.49 g (2.6 mmol, 1.18 eq.) of EDC.HCl and 0.26 g (2.6 mmol, 1.27 eq.) of TEA were suspended in THF (4 mL). While the suspension was cooled in an ice bath, a solution of 0.53 g (2.1 mmol) of Boc-Leu-OH.H$_2$O in THF (4 mL) was added. The mixture was stirred under cooling in the ice bath overnight. Ethyl acetate (5 mL) was added to induce the precipitation of crystals at an internal temperature of 2° C. The precipitated crystals were filtered off. The filtrate was concentrated under reduced pressure and the residue was purified by silica gel chromatography to give 1.43 g of Boc-Leu-Arg(Pbf)-OMe as a white solid (quantitative yield).

$^1$H NMR (400 MHz, CDCl$_3$) δ ppm: 0.93 (d, J=6.4 Hz, 3H); 0.95 (d, J=6.4 Hz, 3H); 1.42 (s, 9H); 1.46 (s, 6H); 1.4-1.8 (m, 6H); 1.8-2.0 (m, 1H); 2.09 (s, 3H); 2.53 (s, 3H); 2.59 (s, 3H); 2.95 (s, 2H); 3.1-3.3 (br. s, 2H); 3.74 (s, 3H); 4.0-4.2 (m, 1H); 4.55 (dt, J1=8.3 Hz, J2=4.5 Hz, 1H); 5.13 (d, J=6.8 Hz, 1H); 6.06, 6.15 (br. s×2, 3H); 7.03 (d. J=8.0 Hz, 1H).

(3) Preparation of Fmoc-Asp(Ot-Bu)-Leu-Arg(Pbf)-OMe

In a 30 mL reaction container, 2.19 g of 5.88% HCl/MeOH (3.53 mmol) was added to 1.20 g (1.76 mmol) of Boc-Leu-Arg(Pbf)-OMe. The mixture was stirred at an internal temperature of 41 to 43° C. overnight and was further stirred at room temperature for two days. The mixture was concentrated under reduced pressure. To the residue, THF (1 mL) was added, and the solution was concentrated for replacement. THF (3 mL) was added and the mixture was transferred to a 100 mL reaction container. To the mixture were successively added 0.74 g (1.8 mmol, 1.03 eq.) of Fmoc-Asp(Ot-Bu)—OH, 0.24 g (1.8 mmol, 1.02 eq.) of HOBt and 0.39 g (2.0 mmol, 1.16 eq.) of EDC.HCl to produce a suspension. While the suspension was cooled in an ice bath, 0.41 mL (3.7 mmol, 2.13 eq.) of NMM was added. The mixture was stirred under cooling in the ice bath overnight. Ethyl acetate (6 mL) was added to induce the precipitation of crystals. The precipitated crystals were filtered off. The filtrate was concentrated under reduced pressure and the residue was purified by silica gel column chromatography to give 1.28 g of Fmoc-Asp(Ot-Bu)-Leu-Arg(Pbf)-OMe as a white solid (99.9% two-step yield from Boc-Leu-Arg(Pbf)-OMe).

$^1$H NMR (400 MHz, CDCl$_3$) δ ppm: 0.88 (d, J=5.6 Hz, 3H); 0.93 (d, J=6.0 Hz, 3H); 1.44 (s, 9H); 1.44 (s, 6H); 1.4-1.9 (m, 7H); 2.08 (s, 3H); 2.52 (s, 3H); 2.58 (s, 3H); 2.66 (dd, J1=17.1 Hz, J2=4.9 Hz, 1H); 2.88 (dd, J1=17.1 Hz, J2=3.6 Hz, 1H); 2.93 (s, 2H); 3.19 (br. s, 2H); 3.70 (s, 3H); 4.21 (t, J=6.6 Hz, 1H); 4.43 (d, J=6.4 Hz, 1H); 4.4-4.5 (br. s, 1H); 4.57 (dt, J1=8.5 Hz, J2=4.1 Hz, 1H); 5.8, 6.10 (br. s×2, 3H); 6.0-6.2 (br. s, 1H); 6.8-6.9 (m, 1H); 7.31 (t, J=7.6 Hz, 1H); 7.41 (t, J=7.6 Hz, 1H); 7.57 (d, J=7.6 Hz, 1H); 7.77 (d, J=7.6 Hz, 1H).

(4) Deprotection of N-Terminus to Give Hydrochloric Acid Salt of Peptide Derivative VIa:

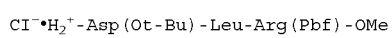

In a 50 mL reaction container, THF (1.6 mL) was added to 0.74 g (1.09 mmol) of Fmoc-Asp(Ot-Bu)-Leu-Arg(Pbf)-OMe to produce a solution. To the solution, 0.21 mL (2.1 mmol, 1.94 eq.) of piperidine was added, and the mixture was stirred at room temperature overnight. Ethyl acetate (2 mL) and tap water (4 mL) were added to induce the precipitation of a white solid. The precipitated crystals were filtered off. To the filtrate, ethyl acetate (3.5 mL) was added and the mixture was stirred and then left to stand. The resulting layers were separated. The cloudy light yellow organic layer was successively washed with 0.5 N hydrochloric acid (1 mL), 1 N hydrochloric acid (1 mL) and 1 N hydrochloric acid (2 mL×2). The organic layer was concentrated under reduced pressure to give 0.71 g of Cl$^-$.H$_2$$^+$-Asp(Ot-Bu)-Leu-Arg(Pbf)-OMe (a hydrochloric acid salt of Peptide derivative VIa) as a light yellow syrup-like residue (86% yield).

$^1$H NMR (400 MHz, CDCl$_3$) δ ppm: 0.90 (d, J=5.6 Hz, 3H); 0.94 (d, J=6.0 Hz, 3H); 1.45 (s, 9H); 1.47 (s, 6H); 1.6-1.9 (m, 7H); 2.10 (s, 3H); 2.49 (s, 3H); 2.55 (s, 3H); 2.97 (s, 2H); 3.06 (dd, J1=19.0 Hz, J2=6.8 Hz, 1H); 3.12 (dd, J1=19.0 Hz, J2=6.4 Hz, 1H); 3.27 (br. s, 2H); 3.70 (s, 3H); 4.3-4.5 (m, 2H); 4.5-4.6 (m, 1H); 6.68 (br. s, 3H); 8.5-8.9 (br. s, 1H); 8.17 (br. s, 1H); 8.58 (br. s, 3H).

Reference Example 3

Synthesis of Peptide Derivative VIb:

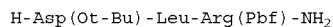

(1) Preparation of Cl$^-$.H$_2$$^+$-Leu-Arg(Pbf)-NH$_2$

In a 100 mL reaction container, 30 mL of an 8 N NH$_3$/MeOH solution (240 mmol) was added to 6.54 g (10 mmol) of Boc-Leu-Arg(Pbf)-OMe. The reaction solution was stirred at room temperature for two days and concentrated under reduced pressure. To the residue, CPME (14.5 mL) was added, and the solution was concentrated for replacement to produce a colorless solution of Boc-Leu-Arg(Pbf)-NH$_2$ in CPME. Separately, in a 100 mL reaction container was placed 10.4 mL of a 4 M HCl/CPME solution (41.6 mmol). While the solution was cooled in an ice bath, the above solution of the synthesized Boc-Leu-Arg(Pbf)-NH$_2$ in CPME was added dropwise. The mixture was stirred at room temperature overnight. Suction filtration was performed and thorough washing with CPME (12.1 mL×2) was performed. Warm air-drying at 40° C. was performed to give 5.68 g of Cl$^-$.H$_2$$^+$-Leu-Arg(Pbf)-NH$_2$ as a white powder (quantitative two-step yield from Boc-Leu-Arg(Pbf)-OMe).

$^1$H NMR (400 MHz, DMSO-d$_6$) δ ppm: 0.8-1.0 (m, 6H); 1.41 (s, 6H); 1.3-1.6 (m, 5H); 1.6-1.8 (m, 2H); 2.01 (s, 3H); 2.43 (s, 3H); 2.49 (s, 3H); 3.0-3.1 (br. s, 2H); 3.8-3.9 (br. s, 1H); 4.2-4.3 (m, 1H); 6.08, 6.54 (br. s×2, 3H); 7.06 (s, 1H); 7.52 (s, 1H); 8.2-8.4 (m, 3H); 8.6-8.7 (m, 1H).

(2) Preparation of Peptide Derivative VIb:

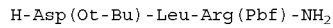

In a 100 mL reaction container were placed 1.02 g (1.77 mmol) of the above synthesized peptide derivative, Cl$^-$.H$_2$$^+$-Leu-Arg(Pbf)-NH$_2$, 0.25 g (1.9 mmol) of HOBt, 0.40 g (2.1 mmol) of EDC.HCl and 0.63 g (1.5 mmol) of Fmoc-Asp(Ot-Bu)—OH. While the mixture was stirred, THF (8 mL) was added. While the mixture was cooled in an ice bath, 0.45 mL (4.1 mmol) of NMM was added. The mixture was stirred under cooling in the ice bath for 5.8 hours. To this, ethyl acetate (8 mL) and tap water (8 mL) were added, and the mixture was stirred at room temperature and then left to stand. The resulting layers were separated. The organic layer was washed successively with a saturated sodium bicarbonate solution (4 mL), tap water (4 mL), 1 N hydrochloric acid (4 mL×twice) and tap water (4 mL×2). To the resulting solution of Fmoc-Asp(Ot-Bu)-Leu-Arg(Pbf)-NH$_2$ in ethyl acetate, 0.36 mL (3.6 mmol, 2.05 eq.) of piperidine was added, and the mixture was stirred at room temperature overnight. To this, tap water (4 mL) was added, and the mixture was stirred and then left to stand. The resulting layers were separated. The organic layer was washed with tap water (4 mL×twice). The organic layer was concentrated under reduced pressure. To the residue was added DMF (2.5 mL) and concentration under reduced pressure was performed again. The precipitated solid was filtered off and the filtrate was dried with a pump to give 0.98 g of H-Asp(Ot-Bu)-Leu-Arg(Pbf)-NH$_2$ (Peptide derivative VIb) (78% two-step yield from Cl$^-$.H$_2^+$-Leu-Arg(Pbf)-NH$_2$).

$^1$H NMR (400 MHz, CDCl$_3$) δ ppm: 0.91 (d, J=6.0 Hz, 3H); 0.96 (d, J=6.0 Hz, 3H); 1.43 (s, 9H); 1.46 (s, 6H); 1.5-1.9 (m, 6H); 1.9-2.0 (m, 1H); 2.09 (s, 3H); 2.51 (s, 3H); 2.58 (s, 3H); 2.5-2.7 (m, 1H); 2.7-2.8 (m, 1H); 2.9-3.0 (s, 2H); 3.2-3.3 (m, 2H); 3.68 (dd, J1=7.2 Hz, J2=4.8 Hz, 2H); 3.7-3.8 (m, 1H); 4.2-4.4 (m, 1H); 4.48 (dt, J1=8.6 Hz, J2=4.7 Hz, 1H); 5.66 (s, 1H); 6.18, 6.28 (br. s×2, 3H); 6.94 (s, 1H); 7.45 (d, J=8.0 Hz, 1H); 7.90 (d, J=6.8 Hz, 1H).

Reference Example 4

Synthesis of Peptide Derivative IIa (X=Ala):

Leu-Ala-Leu-OMe (1) Preparation of Boc-Leu-Ala-Leu-OMe

In a 10 L reaction container were placed 300 g (1.65 mol) of Cl$^-$.H$_2^+$-Leu-OMe, 327 g (1.73 mol) of Boc-Ala-OH, 268 g (1.98 mol) of HOBt and THF (3600 mL). While the mixture was cooled at an internal temperature of −5 to 0° C., 550 mL (3.96 mol) of TEA was added dropwise. To this solution, 380 g (1.98 mol) of EDC.HCl was added. The mixture was stirred under cooling in an ice bath overnight. To the reaction solution were added 9% saline (1500 mL) and ethyl acetate (3000 mL), and the resulting layers were separated. The organic layer was washed successively with a 7% sodium bicarbonate solution (1500 mL×twice), tap water (1500 mL), 1 N hydrochloric acid (1500 mL) and tap water (1500 mL×three times). The organic layer was concentrated under reduced pressure. To the concentrated residue, CPME (1500 mL) was added, and the solution was concentrated for replacement to produce a solution of Boc-Ala-Leu-OMe in CPME. To this, 3300 mL of a 2 M HCl/CPME solution (6.60 mol) was added, and the mixture was stirred at room temperature overnight. The mixture was concentrated under reduced pressure to produce Cl$^-$.H$_2^+$-Ala-Leu-OMe. To this, THF (1800 mL) was added. The mixture was heated to an outside temperature of 40° C., and to the mixture were added 364 g (1.46 mol) of Boc-Leu-OH and 230 g (1.70 mol) of HOBt. While the mixture was cooled at an internal temperature of −5 to 0° C., 326 g (1.70 mol) of EDC.HCl was added, and 470 mL (3.41 mol) of TEA was then added dropwise. The reaction solution was stirred under cooling in the ice bath overnight. To the reaction solution, 9% saline (1800 mL) and isopropyl acetate (3600 mL) were added, and the resulting layers were separated. The organic layer was washed successively with a 7% sodium bicarbonate solution (1800 mL×twice), tap water (1800 mL), 1 N hydrochloric acid (1800 mL) and tap water (1800 mL×three times). The organic layer was filtered and the filtrate was concentrated. The concentrated residue was recrystallized from IPA (1000 mL). The crystals were separated by filtration and dissolved in a MTBE/IPA (9/1) mixed solution (4800 mL), and insoluble matter was filtered off. The filtrate was concentrated under reduced pressure and the residue was recrystallized from IPA (912 mL). The crystals were separated by filtration and vacuum dried to give 294 g of Boc-Leu-Ala-Leu-OMe (40% three step-yield from Cl$^-$.H$_2^+$-Leu-OMe).

$^1$H NMR (400 MHz, CDCl$_3$) δ ppm: 0.9-1.0 (m, 12H); 1.38 (d, J=7.2 Hz, 3H); 1.44 (s, 9H); 1.5-1.7 (m, 6H); 3.73 (s, 3H); 4.09 (br. s, 1H); 4.4-4.6 (m, 2H); 4.86 (br. s, 1H); 6.5-6.7 (m, 2H).

(2) Preparation of Hydrochloric Acid Salt of Peptide Derivative IIa (X=Ala):

Cl$^-$•H$_2^+$-Leu-Ala-Leu-OMe

In a 5 L reaction container were placed 250 g (0.56 mol) of Boc-Leu-Ala-Leu-OMe and 1160 mL of a 2 M HCl/CPME solution (2.32 mol). The mixture was stirred at room temperature overnight. To this, IPE (1250 mL) was added and the mixture was stirred for 10 minutes. The supernatant was discarded by decantation. After addition of IPE (3000 mL), the mixture was stirred for 10 minutes. The supernatant was discarded by decantation. Concentration under reduced pressure was performed to give 199 g of Cl$^-$.H$_2^+$-Leu-Ala-Leu-OMe (a hydrochloric acid salt of Peptide derivative IIa (X=Ala)) (96.3% yield).

$^1$H NMR (400 MHz, CDCl$_3$) δ ppm: 0.90-0.97 (m, 12H); 1.42 (d, J=6.8 Hz, 3H); 1.63-1.82 (m, 6H); 3.71 (s, 3H); 4.38 (br. s, 1H); 4.47-4.50 (m, 1H); 4.71 (br. s, 1H); 7.59 (br. s, 1H); 8.28 (br. s, 3H); 8.51 (br. s, 1H).

Reference Example 5

Synthesis of Hydrochloric Acid Salt of Peptide Derivative IIa (X=Leu):

Cl$^-$•H$_2^+$-Leu-Leu-Leu-OMe

In a 30 mL reaction container was placed 1.00 g (2.80 mmol) of H-Leu-Leu-Leu-OH. To this, 5 mL of a 2 M HCl/MeOH solution (10 mmol) was added, and the mixture was stirred at room temperature overnight. The mixture was concentrated under reduced pressure to give 1.17 g of Cl$^-$.H$_2^+$-Leu-Leu-Leu-OMe (a hydrochloric acid salt of Peptide derivative IIa (X=Leu)) (quantitative yield).

$^1$H NMR (400 MHz, D$_2$O) δ ppm: 0.82 (d, J=6.6 Hz, 3H); 0.83-0.90 (m, 12H); 0.92 (d, J=6.6 Hz, 3H); 1.3-1.8 (m, 9H); 3.5-3.7 (s, 3H); 3.6-3.9 (m, 1H); 4.2-4.4 (m, 1H); 4.4-4.5 (m, 1H); 8.14 (br. s, 3H); 8.46 (d, J=7.8 Hz, 1H); 8.61 (d, J=8.4 Hz, 1H).

Thus produced self-assembling peptide derivatives of the present invention are used in accordance with known technical standards.

INDUSTRIAL APPLICABILITY

The present invention enables the production of self-assembling peptide derivatives that are useful in the fields of regenerative medicine and surgery, at a low cost and in an efficient manner. The production is also easy to scale up.

The invention claimed is:

1. A disulfuric acid salt of a peptide derivative, represented by general formula (IX):

(SEQ ID NO: 4)
Ac-Arg-Leu-Asp-Leu-Arg-Leu-Ala-Leu-Arg-Leu-Asp-

Leu-Arg-NH$_2$•2H$_2$SO$_4$ or general formula (X):

(SEQ ID NO: 5)
Ac-Arg-Leu-Asp-Leu-Arg-Leu-Leu-Leu-Arg-Leu-Asp-

Leu-Arg-NH$_2$•2H$_2$SO$_4$.

2. A process for producing a tetrahydrochloric acid salt of a peptide derivative represented by general formula (XI):

(SEQ ID NO: 9)
Ac-Arg-Leu-Asp-Leu-Arg-Leu-Ala-Leu-Arg-Leu-Asp-

Leu-Arg-NH$_2$•4HCl or general formula (XII):

(SEQ ID NO: 10)
Ac-Arg-Leu-Asp-Leu-Arg-Leu-Leu-Leu-Arg-Leu-Asp-

Leu-Arg-NH$_2$•4HCl, the process comprising the step of performing a salt exchange reaction of a peptide derivative represented by general formula (IX):

(SEQ ID NO: 4)
Ac-Arg-Leu-Asp-Leu-Arg-Leu-Ala-Leu-Arg-Leu-Asp-

Leu-Arg-NH$_2$•2H$_2$SO$_4$ and/or general formula (X):

(SEQ ID NO: 5)
Ac-Arg-Leu-Asp-Leu-Arg-Leu-Leu-Leu-Arg-Leu-Asp-

Leu-Arg-NH$_2$•2H$_2$SO$_4$ by treating the peptide derivative with hydrochloric acid in the presence of an organic solvent.

3. The production process according to claim 2, wherein the organic solvent is THF.

4. The production process according to claim 2 comprising a process for producing the peptide derivative represented by general formula (IX)

or general formula (X)

the process comprising the steps of forming as building blocks, Peptide derivative I represented by general formula (I):

Arg(protecting group A)-Leu-Asp(protecting group B)-Leu-Arg(protecting group C) (SEQ ID NO: 8)

(wherein protecting group A and protecting group C may be the same or different, and each is an Arg side-chain protecting group that is stable under basic conditions, can be removed under highly acidic conditions, and is selected from sulfonyl groups;

protecting group B is an Asp side-chain protecting group that is stable under basic conditions and can be removed under highly acidic conditions; and the amino group of the N-terminal Arg and/or the carboxy group of the C-terminal Arg may be modified) and Peptide derivative II represented by general formula (II):

Leu-X-Leu (wherein the amino group of the N-terminal Leu and/or the carboxy group of the C-terminal Leu may be modified; and X is Ala or Leu), serially coupling, said building blocks removing the side-chain protecting groups with a 75 to 98 vol % aqueous TFA solution containing no scavenger except water, and optionally subjecting the coupling product to a terminal deprotection step and/or a modification step.

5. The production process according to claim 4, comprising the steps of coupling Peptide derivative Ia corresponding to Peptide derivative I having an acetylated N-terminus with Peptide derivative IIa corresponding to Peptide derivative II having the C-terminus protected by an ester group to yield Peptide derivative IIIa, deprotecting the C-terminus of Peptide derivative IIIa, coupling the deprotected Peptide derivative IIIa with Peptide derivative Ib corresponding to Peptide derivative I having an amidated C-terminus to yield Peptide derivative IVa, and removing the side-chain protecting groups from Peptide derivative IVa.

6. The production process according to claim 4, comprising the steps of coupling Peptide derivative Ia corresponding to Peptide derivative I having an acetylated N-terminus with Peptide derivative IIa corresponding to Peptide derivative II having the C-terminus protected by an ester group to yield Peptide derivative IIIa, deprotecting the C-terminus of Peptide derivative IIIa, coupling the deprotected Peptide derivative IIIa with Peptide derivative Ic corresponding Peptide derivative I having the C-terminus protected by an ester group to yield Peptide derivative IVb, removing the side-chain protecting groups from Peptide derivative IVb, and converting the C-terminal ester group to an amide group.

7. The production process according to claim 5, wherein the C-terminal ester of Peptide derivative IIa is a methyl ester.

8. The production process according to claim 6, wherein the C-terminal ester of Peptide derivative IIa is a methyl ester.

9. The production process according to claim 6, wherein the C-terminal ester of Peptide derivative Ic is a methyl ester.

10. The production process according to claim 4 comprising the step of preparing Peptide derivative I by coupling Peptide derivative V represented by general formula (V):

Arg(protecting group A)-Leu (wherein protecting group A is as defined above, and the amino group of the N-terminal Arg is modified) with Peptide derivative VI represented by general formula (VI):

Asp(protecting group B)-Leu-Arg(protecting group C)

(wherein protecting groups B and C are as defined above, and the carboxy group of the C-terminal Arg is modified), and optionally subjecting the resulting coupling product to a deprotection step and/or a modification step of the amino group of the N-terminal Arg and/or the carboxy group of the C-terminal Arg.

11. The production process according to claim 4 wherein protecting groups A and C are each a 2, 2, 4, 6, 7-pentamethyl-2,3-dihydrobenzofuran-5-sulfonyl group.

12. The production process according to claim 4 wherein protecting group B is a t-butyl ester.

13. The production process according to claim 10 comprising the step of preparing Peptide derivative Ia corresponding to Peptide derivative I having an acetylated N-terminus by coupling Peptide derivative Va corresponding to Peptide derivative V having an acetylated N-terminus with Peptide derivative VIa corresponding to Peptide derivative VI having the C-terminus protected by an ester group, and removing the C-terminal ester; and/or the step of preparing Peptide derivative Ia by coupling Peptide derivative Vb corresponding to Peptide derivative V having the N-terminus protected by a protecting group other than an acetyl group with Peptide derivative VIa, converting the N-terminal group to an acetyl group, and removing the C-terminal ester.

14. The production process according to claim 13, wherein the C-terminal ester of Peptide derivative VIa is a methyl ester.

15. The production process according to claim 10 comprising the step of preparing Peptide derivative Ib corresponding to Peptide derivative I having an amidated C-terminus by coupling Peptide derivative Vb corresponding to Peptide derivative V having the N-terminus protected by a protecting group other than an acetyl group with Peptide derivative VIb corresponding to Peptide derivative VI having an amidated C-terminus, and deprotecting the N-terminus of the resulting coupling product.

16. The production process according to claim 10 comprising the step of preparing Peptide derivative Ic corresponding to Peptide derivative I having the C-terminus protected by an ester group by coupling Peptide derivative Vb corresponding to Peptide derivative V having the N-terminus protected by a protecting group other than an acetyl group with Peptide derivative VIa corresponding to Peptide derivative VI having the C-terminus protected by an ester group, and deprotecting the N-terminus of the resulting coupling product.

* * * * *

SEQUENCE LISTING

<160> NUMBER OF SEQ ID NOS: 28

<210> SEQ ID NO 1
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
<220> FEATURE:
<221> NAME/KEY: MISC_FEATURE
<222> LOCATION: (13)..(13)
<223> OTHER INFORMATION: Modified with an Amidogen

<400> SEQUENCE: 1

Arg Leu Asp Leu Arg Leu Ala Leu Arg Leu Asp Leu Arg
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
<220> FEATURE:
<221> NAME/KEY: MISC_FEATURE
<222> LOCATION: (13)..(13)
<223> OTHER INFORMATION: Modified with an Amidogen

<400> SEQUENCE: 2

Arg Leu Asp Leu Arg Leu Leu Leu Arg Leu Asp Leu Arg
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 3

Arg Leu Asp Leu Arg
1               5

<210> SEQ ID NO 4
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
<220> FEATURE:
<221> NAME/KEY: MISC_FEATURE
<222> LOCATION: (13)..(13)
<223> OTHER INFORMATION: Modified with an Amidogen Disulfuric Acid Sald

<400> SEQUENCE: 4

Arg Leu Asp Leu Arg Leu Ala Leu Arg Leu Asp Leu Arg
1               5                   10

```
<210> SEQ ID NO 5
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
<220> FEATURE:
<221> NAME/KEY: MISC_FEATURE
<222> LOCATION: (13)..(13)
<223> OTHER INFORMATION: Modified with an Amidogen Disulfuric Acid Salt

<400> SEQUENCE: 5

Arg Leu Asp Leu Arg Leu Leu Leu Arg Leu Asp Leu Arg
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
<220> FEATURE:
<221> NAME/KEY: MISC_FEATURE
<222> LOCATION: (13)..(13)
<223> OTHER INFORMATION: Modified with an Amdiogen and "n"

<400> SEQUENCE: 6

Arg Leu Asp Leu Arg Leu Ala Leu Arg Leu Asp Leu Arg
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
<220> FEATURE:
<221> NAME/KEY: MISC_FEATURE
<222> LOCATION: (13)..(13)
<223> OTHER INFORMATION: Modified with an Amidogen and "n"

<400> SEQUENCE: 7

Arg Leu Asp Leu Arg Leu Leu Leu Arg Leu Asp Leu Arg
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with Protecting group A
<220> FEATURE:
<221> NAME/KEY: MISC_FEATURE
<222> LOCATION: (3)..(3)
<223> OTHER INFORMATION: Modified with protecting Group B
<220> FEATURE:
<221> NAME/KEY: MISC_FEATURE
```

<222> LOCATION: (5)..(5)
<223> OTHER INFORMATION: Modified with Protecting Group C

<400> SEQUENCE: 8

Arg Leu Asp Leu Arg
1               5

<210> SEQ ID NO 9
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
<220> FEATURE:
<221> NAME/KEY: MISC_FEATURE
<222> LOCATION: (13)..(13)
<223> OTHER INFORMATION: Modified with tetrahydrochloric acid salt

<400> SEQUENCE: 9

Arg Leu Asp Leu Arg Leu Ala Leu Arg Leu Asp Leu Arg
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
<220> FEATURE:
<221> NAME/KEY: MISC_FEATURE
<222> LOCATION: (10)..(10)
<223> OTHER INFORMATION: Modified with tetrahydrochloric acid salt

<400> SEQUENCE: 10

Arg Leu Asp Leu Arg Leu Leu Leu Arg Leu Asp Leu Arg
1               5                   10

<210> SEQ ID NO 11
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
<220> FEATURE:
<221> NAME/KEY: MISC_FEATURE
<222> LOCATION: (1)..(1)
<223> OTHER INFORMATION: Modified with
      2,2,4,6,7-pentamethyl-2,3-dihydrobenzofuran-5-sulfonyl
<220> FEATURE:
<221> NAME/KEY: MISC_FEATURE
<222> LOCATION: (3)..(3)
<223> OTHER INFORMATION: Modified with tert-butyl ester
<220> FEATURE:
<221> NAME/KEY: MISC_FEATURE
<222> LOCATION: (5)..(5)
<223> OTHER INFORMATION: Modified with
      2,2,4,6,7-pentamethyl-2,3-dihydrobenzofuran-5-sulfonyl
<220> FEATURE:
<221> NAME/KEY: MISC_FEATURE
<222> LOCATION: (5)..(5)
<223> OTHER INFORMATION: Modified with a Hydroxide -continued

<400> SEQUENCE: 11

Arg Leu Asp Leu Arg
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
<220> FEATURE:
<221> NAME/KEY: MISC_FEATURE
<222> LOCATION: (1)..(1)
<223> OTHER INFORMATION: Modified with
      2,2,4,6,7-pentamethyl-2,3-dihydrobenzofuran-5-sulfonyl
<220> FEATURE:
<221> NAME/KEY: MISC_FEATURE
<222> LOCATION: (3)..(3)
<223> OTHER INFORMATION: Modified with tert-butyl ester
<220> FEATURE:
<221> NAME/KEY: MISC_FEATURE
<222> LOCATION: (5)..(5)
<223> OTHER INFORMATION: Modified with
      2,2,4,6,7-pentamethyl-2,3-dihydrobenzofuran-5-sulfonyl
<220> FEATURE:
<221> NAME/KEY: MISC_FEATURE
<222> LOCATION: (8)..(8)
<223> OTHER INFORMATION: Modified with  methyl ester

<400> SEQUENCE: 12

Arg Leu Asp Leu Arg Leu Ala Leu
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
<220> FEATURE:
<221> NAME/KEY: MISC_FEATURE
<222> LOCATION: (1)..(1)
<223> OTHER INFORMATION: Modified with
      2,2,4,6,7-pentamethyl-2,3-dihydrobenzofuran-5-sulfonyl
<220> FEATURE:
<221> NAME/KEY: MISC_FEATURE
<222> LOCATION: (3)..(3)
<223> OTHER INFORMATION: Modified with tert-butyl ester
<220> FEATURE:
<221> NAME/KEY: MISC_FEATURE
<222> LOCATION: (5)..(5)
<223> OTHER INFORMATION: Modified with
      2,2,4,6,7-pentamethyl-2,3-dihydrobenzofuran-5-sulfonyl
<220> FEATURE:
<221> NAME/KEY: MISC_FEATURE
<222> LOCATION: (8)..(8)
<223> OTHER INFORMATION: Modified with a Hydroxide

<400> SEQUENCE: 13

Arg Leu Asp Leu Arg Leu Ala Leu
1               5

<210> SEQ ID NO 14
<211> LENGTH: 13

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
<220> FEATURE:
<221> NAME/KEY: MISC_FEATURE
<222> LOCATION: (1)..(1)
<223> OTHER INFORMATION: Modified with
     2,2,4,6,7-pentamethyl-2,3-dihydrobenzofuran-5-sulfonyl
<220> FEATURE:
<221> NAME/KEY: MISC_FEATURE
<222> LOCATION: (3)..(3)
<223> OTHER INFORMATION: Modified with tert-butyl ester
<220> FEATURE:
<221> NAME/KEY: MISC_FEATURE
<222> LOCATION: (5)..(5)
<223> OTHER INFORMATION: Modified with
     2,2,4,6,7-pentamethyl-2,3-dihydrobenzofuran-5-sulfonyl
<220> FEATURE:
<221> NAME/KEY: MISC_FEATURE
<222> LOCATION: (9)..(9)
<223> OTHER INFORMATION: Modified with
     2,2,4,6,7-pentamethyl-2,3-dihydrobenzofuran-5-sulfonyl
<220> FEATURE:
<221> NAME/KEY: MISC_FEATURE
<222> LOCATION: (11)..(11)
<223> OTHER INFORMATION: Modified with tert-butyl ester
<220> FEATURE:
<221> NAME/KEY: MISC_FEATURE
<222> LOCATION: (13)..(13)
<223> OTHER INFORMATION: Modified with
     2,2,4,6,7-pentamethyl-2,3-dihydrobenzofuran-5-sulfonyl
<220> FEATURE:
<221> NAME/KEY: MISC_FEATURE
<222> LOCATION: (13)..(13)
<223> OTHER INFORMATION: Modified with an Amidogen

<400> SEQUENCE: 14

Arg Leu Asp Leu Arg Leu Ala Leu Arg Leu Asp Leu Arg
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
<220> FEATURE:
<221> NAME/KEY: MISC_FEATURE
<222> LOCATION: (13)..(13)
<223> OTHER INFORMATION: Modified with an Amidogen and 4 MsOH
     (methanesulfonic acid)

<400> SEQUENCE: 15

Arg Leu Asp Leu Arg Leu Ala Leu Arg Leu Asp Leu Arg
1               5                   10

<210> SEQ ID NO 16
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
```

```
<220> FEATURE:
<221> NAME/KEY: MISC_FEATURE
<222> LOCATION: (1)..(1)
<223> OTHER INFORMATION: Modified with
      2,2,4,6,7-pentamethyl-2,3-dihydrobenzofuran-5-sulfonyl
<220> FEATURE:
<221> NAME/KEY: MISC_FEATURE
<222> LOCATION: (3)..(3)
<223> OTHER INFORMATION: Modified with tert-butyl ester
<220> FEATURE:
<221> NAME/KEY: MISC_FEATURE
<222> LOCATION: (5)..(5)
<223> OTHER INFORMATION: Modified with
      2,2,4,6,7-pentamethyl-2,3-dihydrobenzofuran-5-sulfonyl; MsOH is
      methanesulfonic acid
<220> FEATURE:
<221> NAME/KEY: MISC_FEATURE
<222> LOCATION: (8)..(8)
<223> OTHER INFORMATION: Modified with methyl ester

<400> SEQUENCE: 16

Arg Leu Asp Leu Arg Leu Leu Leu
1               5

<210> SEQ ID NO 17
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
<220> FEATURE:
<221> NAME/KEY: MISC_FEATURE
<222> LOCATION: (1)..(1)
<223> OTHER INFORMATION: Modified with
      2,2,4,6,7-pentamethyl-2,3-dihydrobenzofuran-5-sulfonyl
<220> FEATURE:
<221> NAME/KEY: MISC_FEATURE
<222> LOCATION: (3)..(3)
<223> OTHER INFORMATION: Modified with tert-butyl ester
<220> FEATURE:
<221> NAME/KEY: MISC_FEATURE
<222> LOCATION: (5)..(5)
<223> OTHER INFORMATION: 2,2,4,6,7-pentamethyl-2,3-dihydrobenzofuran-
      5-sulfonyl
<220> FEATURE:
<221> NAME/KEY: MISC_FEATURE
<222> LOCATION: (9)..(9)
<223> OTHER INFORMATION: Modified with
      2,2,4,6,7-pentamethyl-2,3-dihydrobenzofuran-5-sulfonyl
<220> FEATURE:
<221> NAME/KEY: MISC_FEATURE
<222> LOCATION: (11)..(11)
<223> OTHER INFORMATION: Modified with tert-butyl ester
<220> FEATURE:
<221> NAME/KEY: MISC_FEATURE
<222> LOCATION: (13)..(13)
<223> OTHER INFORMATION: Modified with
      2,2,4,6,7-pentamethyl-2,3-dihydrobenzofuran-5-sulfonyl
<220> FEATURE:
<221> NAME/KEY: MISC_FEATURE
<222> LOCATION: (13)..(13)
<223> OTHER INFORMATION: Modified with an Amidogen

<400> SEQUENCE: 17

Arg Leu Asp Leu Arg Leu Leu Leu Arg Leu Asp Leu Arg
1               5                   10

<210> SEQ ID NO 18
<211> LENGTH: 13
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
<220> FEATURE:
<221> NAME/KEY: MISC_FEATURE
<222> LOCATION: (3)..(3)
<223> OTHER INFORMATION: Modified with tert-butyl ester
<220> FEATURE:
<221> NAME/KEY: MISC_FEATURE
<222> LOCATION: (5)..(5)
<223> OTHER INFORMATION: Modified with
     2,2,4,6,7-pentamethyl-2,3-dihydrobenzofuran-5-sulfonyl
<220> FEATURE:
<221> NAME/KEY: MISC_FEATURE
<222> LOCATION: (9)..(9)
<223> OTHER INFORMATION: Modified with
     2,2,4,6,7-pentamethyl-2,3-dihydrobenzofuran-5-sulfonyl
<220> FEATURE:
<221> NAME/KEY: MISC_FEATURE
<222> LOCATION: (11)..(11)
<223> OTHER INFORMATION: Modified with tert-butyl ester
<220> FEATURE:
<221> NAME/KEY: MISC_FEATURE
<222> LOCATION: (13)..(13)
<223> OTHER INFORMATION: Modified with
     2,2,4,6,7-pentamethyl-2,3-dihydrobenzofuran-5-sulfonyl
<220> FEATURE:
<221> NAME/KEY: MISC_FEATURE
<222> LOCATION: (13)..(13)
<223> OTHER INFORMATION: Modified with methyl ester

<400> SEQUENCE: 18

Arg Leu Asp Leu Arg Leu Ala Leu Arg Leu Asp Leu Arg
1               5                   10

<210> SEQ ID NO 19
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with Cl-H2+
<220> FEATURE:
<221> NAME/KEY: MISC_FEATURE
<222> LOCATION: (1)..(1)
<223> OTHER INFORMATION: Modified with
     2,2,4,6,7-pentamethyl-2,3-dihydrobenzofuran-5-sulfonyl
<220> FEATURE:
<221> NAME/KEY: MISC_FEATURE
<222> LOCATION: (3)..(3)
<223> OTHER INFORMATION: Modified with tert-butyl ester
<220> FEATURE:
<221> NAME/KEY: MISC_FEATURE
<222> LOCATION: (5)..(5)
<223> OTHER INFORMATION: Modified with
     2,2,4,6,7-pentamethyl-2,3-dihydrobenzofuran-5-sulfonyl
<220> FEATURE:
<221> NAME/KEY: MISC_FEATURE
<222> LOCATION: (5)..(5)
<223> OTHER INFORMATION: Modified with methyl ester

<400> SEQUENCE: 19

Arg Leu Asp Leu Arg
1               5

<210> SEQ ID NO 20
<211> LENGTH: 13
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
<220> FEATURE:
<221> NAME/KEY: MISC_FEATURE
<222> LOCATION: (13)..(13)
<223> OTHER INFORMATION: Modified with methyl ester and disulfuric acid
      salt

<400> SEQUENCE: 20

Arg Leu Asp Leu Arg Leu Ala Leu Arg Leu Asp Leu Arg
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
<220> FEATURE:
<221> NAME/KEY: MISC_FEATURE
<222> LOCATION: (13)..(13)
<223> OTHER INFORMATION: Modified with and Amidogen and 4TFA
      (trifluoroacetic acid)

<400> SEQUENCE: 21

Arg Leu Asp Leu Arg Leu Ala Leu Arg Leu Asp Leu Arg
1               5                   10

<210> SEQ ID NO 22
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with 9-fluorenylmethyloxycarbonyl
<220> FEATURE:
<221> NAME/KEY: MISC_FEATURE
<222> LOCATION: (1)..(1)
<223> OTHER INFORMATION: Modified with
      2,2,4,6,7-pentamethyl-2,3-dihydrobenzofuran-5-sulfonyl
<220> FEATURE:
<221> NAME/KEY: MISC_FEATURE
<222> LOCATION: (3)..(3)
<223> OTHER INFORMATION: Modified with tert-butyl ester
<220> FEATURE:
<221> NAME/KEY: MISC_FEATURE
<222> LOCATION: (5)..(5)
<223> OTHER INFORMATION: Modified with
      2,2,4,6,7-pentamethyl-2,3-dihydrobenzofuran-5-sulfonyl
<220> FEATURE:
<221> NAME/KEY: MISC_FEATURE
<222> LOCATION: (5)..(5)
<223> OTHER INFORMATION: Modified with methyl ester

<400> SEQUENCE: 22

Arg Leu Asp Leu Arg
1               5

<210> SEQ ID NO 23
<211> LENGTH: 5
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
<220> FEATURE:
<221> NAME/KEY: MISC_FEATURE
<222> LOCATION: (1)..(1)
<223> OTHER INFORMATION: Modified with
     2,2,4,6,7-pentamethyl-2,3-dihydrobenzofuran-5-sulfonyl
<220> FEATURE:
<221> NAME/KEY: MISC_FEATURE
<222> LOCATION: (3)..(3)
<223> OTHER INFORMATION: Modified with tert-butyl ester
<220> FEATURE:
<221> NAME/KEY: MISC_FEATURE
<222> LOCATION: (5)..(5)
<223> OTHER INFORMATION: Modified with
     2,2,4,6,7-pentamethyl-2,3-dihydrobenzofuran-5-sulfonyl
<220> FEATURE:
<221> NAME/KEY: MISC_FEATURE
<222> LOCATION: (5)..(5)
<223> OTHER INFORMATION: Modified with methyl ester

<400> SEQUENCE: 23

Arg Leu Asp Leu Arg
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with 9-fluorenylmethyloxycarbonyl
<220> FEATURE:
<221> NAME/KEY: MISC_FEATURE
<222> LOCATION: (1)..(1)
<223> OTHER INFORMATION: Modified with
     2,2,4,6,7-pentamethyl-2,3-dihydrobenzofuran-5-sulfonyl
<220> FEATURE:
<221> NAME/KEY: MISC_FEATURE
<222> LOCATION: (3)..(3)
<223> OTHER INFORMATION: Modified with tert-butyl ester
<220> FEATURE:
<221> NAME/KEY: MISC_FEATURE
<222> LOCATION: (5)..(5)
<223> OTHER INFORMATION: Modified with
     2,2,4,6,7-pentamethyl-2,3-dihydrobenzofuran-5-sulfonyl
<220> FEATURE:
<221> NAME/KEY: MISC_FEATURE
<222> LOCATION: (5)..(5)
<223> OTHER INFORMATION: Modified with an Amidogen

<400> SEQUENCE: 24

Arg Leu Asp Leu Arg
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with Cl-H2+
<220> FEATURE:
<221> NAME/KEY: MISC_FEATURE
<222> LOCATION: (1)..(1)
```

```
<223> OTHER INFORMATION: Modified with
      2,2,4,6,7-pentamethyl-2,3-dihydrobenzofuran-5-sulfonyl
<220> FEATURE:
<221> NAME/KEY: MISC_FEATURE
<222> LOCATION: (3)..(3)
<223> OTHER INFORMATION: Modified with tert-butyl ester
<220> FEATURE:
<221> NAME/KEY: MISC_FEATURE
<222> LOCATION: (5)..(5)
<223> OTHER INFORMATION: Modified with
      2,2,4,6,7-pentamethyl-2,3-dihydrobenzofuran-5-sulfonyl
<220> FEATURE:
<221> NAME/KEY: MISC_FEATURE
<222> LOCATION: (5)..(5)
<223> OTHER INFORMATION: Modified with an Amdiogen

<400> SEQUENCE: 25

Arg Leu Asp Leu Arg
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with Protecting Group A
<220> FEATURE:
<221> NAME/KEY: MISC_FEATURE
<222> LOCATION: (3)..(3)
<223> OTHER INFORMATION: Modified with Protecting Group B
<220> FEATURE:
<221> NAME/KEY: MISC_FEATURE
<222> LOCATION: (5)..(5)
<223> OTHER INFORMATION: Modified with Protecting Group C
<220> FEATURE:
<221> NAME/KEY: MISC_FEATURE
<222> LOCATION: (7)..(7)
<223> OTHER INFORMATION: Xaa is  Ala or Leu

<400> SEQUENCE: 26

Arg Leu Asp Leu Arg Leu Xaa Leu
1               5

<210> SEQ ID NO 27
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
<220> FEATURE:
<221> NAME/KEY: MISC_FEATURE
<222> LOCATION: (7)..(7)
<223> OTHER INFORMATION: Xaa is Ala or Leu
<220> FEATURE:
<221> NAME/KEY: MISC_FEATURE
<222> LOCATION: (13)..(13)
<223> OTHER INFORMATION: Modified with an Amidogen

<400> SEQUENCE: 27

Arg Leu Asp Leu Arg Leu Xaa Leu Arg Leu Asp Leu Arg
1               5                   10

<210> SEQ ID NO 28
<211> LENGTH: 8
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with an Acetyl Group
<220> FEATURE:
<221> NAME/KEY: MISC_FEATURE
<222> LOCATION: (1)..(1)
<223> OTHER INFORMATION: Modified with
     2,2,4,6,7-pentamethyl-2,3-dihydrobenzofuran-5-sulfonyl
<220> FEATURE:
<221> NAME/KEY: MISC_FEATURE
<222> LOCATION: (3)..(3)
<223> OTHER INFORMATION: Modified with tert-butyl ester
<220> FEATURE:
<221> NAME/KEY: MISC_FEATURE
<222> LOCATION: (5)..(5)
<223> OTHER INFORMATION: Modified with
     2,2,4,6,7-pentamethyl-2,3-dihydrobenzofuran-5-sulfonyl
<220> FEATURE:
<221> NAME/KEY: MISC_FEATURE
<222> LOCATION: (8)..(8)
<223> OTHER INFORMATION: Modified with a Hydroxide

<400> SEQUENCE: 28

Arg Leu Asp Leu Arg Leu Leu Leu
1               5
```

UNITED STATES PATENT AND TRADEMARK OFFICE
CERTIFICATE OF CORRECTION

PATENT NO. : 9,963,483 B2  
APPLICATION NO. : 14/412190  
DATED : May 8, 2018  
INVENTOR(S) : Hidenori Yokoi et al.

Page 1 of 1

It is certified that error appears in the above-identified patent and that said Letters Patent is hereby corrected as shown below:

In the Claims

At Column 51, Line 56, "4HCl" should be -- 4HCl --.

At Column 51, Line 62, "4HCl," should be -- 4HCl, --.

Signed and Sealed this
Second Day of October, 2018

Andrei Iancu
*Director of the United States Patent and Trademark Office*